(12) United States Patent
Potter et al.

(10) Patent No.: US 7,968,561 B2
(45) Date of Patent: Jun. 28, 2011

(54) STEROIDAL COMPOUNDS AS STEROID SULPHATASE INHIBITORS

(75) Inventors: Barry Victor Lloyd Potter, Slough (GB); Michael John Reed, Slough (GB); Lok Wai Lawrence Woo, Slough (GB); Atul Purohit, Slough (GB); Paul Foster, Slough (GB)

(73) Assignee: Sterix Limited, Slough, Berkshire (GB)

( * ) Notice: Subject to any disclaimer, the term of this patent is extended or adjusted under 35 U.S.C. 154(b) by 0 days.

(21) Appl. No.: 12/200,252

(22) Filed: Aug. 28, 2008

(65) Prior Publication Data

US 2009/0182000 A1 Jul. 16, 2009

Related U.S. Application Data

(63) Continuation-in-part of application No. PCT/GB2007/000686, filed on Feb. 28, 2007.

(30) Foreign Application Priority Data

Mar. 1, 2006 (GB) .................................. 0604142.0

(51) Int. Cl.
*A01N 43/42* (2006.01)
*A61K 31/44* (2006.01)
*C07D 221/18* (2006.01)
*C07D 221/22* (2006.01)

(52) U.S. Cl. ............................................ 514/284; 546/78
(58) Field of Classification Search .................. 514/284; 546/78
See application file for complete search history.

(56) References Cited

U.S. PATENT DOCUMENTS 7,276,513 B2 * 10/2007 Potter et al. .................... 514/284

FOREIGN PATENT DOCUMENTS

| WO | WO 91/13083 | 9/1991 |
| WO | WO 93/05063 | 3/1993 |
| WO | WO 96/15257 | 5/1996 |

(Continued)

OTHER PUBLICATIONS

Yale HL, "The Trifluoromethyl Group in Medicinal Chemistry," Journal of Medicinal and Pharmaceutical Chemistry, 1959, 1(2), 5-11.*

(Continued)

*Primary Examiner* — San-ming Hui
*Assistant Examiner* — Paul Zarek
(74) *Attorney, Agent, or Firm* — Frommer Lawrence & Haug LLP; Sandra Kuzmich; Russell A. Garman

(57) ABSTRACT

There is provided a compound having Formula I

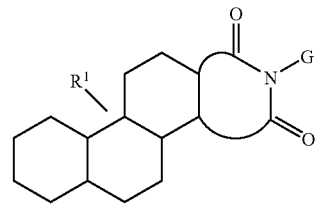

Formula I wherein G is a fluorocarbyl group, and wherein $R^1$ is any one of a sulphamate group, a phosphonate group, a thiophosphonate group, a sulphonate group or a sulphonamide group.

3 Claims, 8 Drawing Sheets

FOREIGN PATENT DOCUMENTS

| WO | WO 98/05635 | 2/1998 |
|---|---|---|
| WO | WO 98/07859 | 2/1998 |
| WO | WO 98/09985 | 3/1998 |
| WO | WO 99/52890 | 10/1999 |
| WO | WO 02/32409 | 4/2002 |
| WO | WO 03/033518 | 4/2003 |

OTHER PUBLICATIONS

Wakefield B, "Fluorinated pharmaceuticals," Innovations in Pharmaceutical Technology, Jan. 2000, 74-77.*

Delphine S. Fischer, et al., D-Ring Modified Estrone Derivatives As Novel Potent Inhibitors of Steroid Sulfatase, Bioorganic & Medicinal Chemistry (2003) vol. 11, p. 1685-1700.

Jerzy Adamski, et al., Molecular Cloning of a Novel Widely Expressed Human 80 kDA 17β-hydroxysteroid Dehydrogenase IV, Biochem. J. (1995) vol. 311, p. 437-443.

D. Agnusdei, et al., Results of International Clinical Trials With Raloxifen, Annales d'Endocrinologie (1999) vol. 60, p. 242-246.

Rolf Appel, et al., Hydrazinesulfonic Acid Amide, Chemische Berichte (1958) vol. 91, p. 1339-1341.

Marion M. Bradford, A Rapid and Sensitive Method for the Quantitation of Microgram Quantities of Protein Utilizing the Principle of Protein-Dye Binding, Analytical Biochemistry (1976) vol. 72, p. 248-254.

Rock Breton, et al., The Structure of a Complex of Human 17β-Hydroxysteroid Dehydrogenase With Estradiol and $NADP^+$ Identifies Two Principal Targets for the Design of Inhibitors, Structure (1996) vol. 4, No. 8, p. 905-915.

M. Castiglione-Gertsch, New Aromatase Inhibitors: More Selectivity, Less Toxicity, Unfortunately, The Same Activity, European Journal of Cancer (1996) vol. 32A, No. 3, p. 393-395.

A. Claussner, et al., 11β-Amidoallcyl Estradiols, A New Series of Pure Antiestrogens, J. Steroid Biochem. Molec. Biol. (1992) vol. 41, No. 3-8, p. 609-614.

N.G. Coldham, et al., A Possible Mechanism for Increased Breast Cell Proliferation by Progestins Through Increased Reductive 17β-Hydroxysteroid Dehydrogenase Activity, Int. J. Cancer (1990) vol. 45, p. 174-178.

Bridgette M. Collins, et al., The Estrogenic and Antiestrogenic Activities of Phytochemicals With the Human Estrogen Receptor Expressed in Yeast, Steroids (1997) vol. 62, p. 365-372.

L. Duncan, et al., Inhibition of Estrone Sulfatase Activity by Estrone-3-Methylthiophosphonate: A Potential Therapeutic Agent in Breast Cancer, J. Cancer Research (1993) vol. 53, p. 298-303.

Wayne M. Geissler, et al., Male Pseudohermaphroditism Caused by Mutations of Testicular 17β-Hydroxysteroid Dehydrogenase 3, Nature Generics (1994) vol. 7, p. 34-39.

Debashis Ghosh, et al., Structure of Human Estrogenic 17β-Hydroxysteroid Dehydrogenase at 2.20 Resolution, Structure (1995) vol. 3, p. 503-513.

Jack Gorski, et al., Current Models of Steroid Hormone Action: A Critique, Annu. Rev. Physiol. (1976) vol. 38, p. 425-450.

Jack Gorski, et al., Hormone Receptors: Studies on the Interaction of Estrogen With the Uterus[1], Recent Progress in Hormone Research (1967) vol. 24, p. 45-80.

Ranju Gupta, et al., Synthesis and Biological Activity of Some D-Ring Modified Estrone Derivatives, Indian Journal of Chemistry (1999) vol. 38B, p. 563-571.

J. Heer, et al., Steroids XL. Marrianolic and Diosynolic Acids. Estrogenic Carboxylic Acids II, Helvetica Chemica Acta (1945) vol. 28, p. 156-65.

K. Holli, et al., Lumpectomy With or Without Postoperative Radiotherapy for Breast Cancer With Favourable Prognostic Features: Results of a Randomized Study, British Journal of Cancer (2001) vol. 84, No. 2, p. 164-169.

Charles A. Horiuchi, et al., Novel regioslective Iodination of Estradiol, Estriol, and Estrone Using Iodine-Copper (II) Acetate, J. Chem. Soc. Chem. Commun. (1982) p. 671-672.

Kathryn B. Horowitz, et al., Nuclear Mechanisms of Estrogen Action, The Journal of Biological Chemistry (1978) vol. 253, No. 22, p. 8185-8193.

Kathryn B. Horowitz, et al., Estrogen Control of Progestrone Receptor in Human Breast Cancer: Role of Estradiol and Antiestrogen*, Endocrinology (1978) vol. 103, p. 1742-1751.

Jiu-Zhen Jin, et al., Human Estrogenic 17β-Hydroxysteroid Dehydrogenase: Predominance of Estrone Reduction and Its Induction by NADPH, Biochemical and Biophysical Research Communications (1999) vol. 259, p. 489-493.

V. Craig Jordan, The Strategic Use of Antiestrogens to Control the Development and Growth of Breast Cancer, Cancer (1992) vol. 70, p. 977-982.

Fernand Labrie, At the Cutting Edge Intracrinology, Molecular and Cellular Endocrinology (1991) vol. 78, p. C113-C118.

J.C. Le Bail, et al., Aromatase and 17β-Hydroxysteroid Dehydrogenase Inhibition by Flavonoids, Cancer Letters (1998) vol. 133, p. 101-106.

Isabelle Le Roy, et al., Genetic Correlation Between Steroid Sulfatase Concentration and Initiation of Attack Behavior in Mice[1], Behavior Genetics (1999) vol. 29, No. 2, p. 131-136.

Pui-Kai Li, et al., Development of Potent Non-Estrogenic Estrone Sulfatase Inhibitors, Steroids (1998) vol. 63, p. 425-432.

Lodish, et al., Cell Division and the Cell Cycle, Molecular Cell Biology (1995) 3rd Edition, p. 177-181.

Bernard Loev, et al., Alkenylphenols Related to the Poison Ivy Principle. An Improved Method of Synthesis Involving the Na-Butanol Cleavage of Benzyl Ethers, J. Am Chem. Soc. (1956) vol. 78, No. 23, p. 6095-6098.

J. H. MacIndoe, et al., The Hydrolysis of Estrone Sulfate and Dehydroepiandrosterone Sulfate by MCF-7 Human Breast Cancer Cells*, Endocrinology (1988) vol. 123, p. 1281-1287.

Mitsuteru Numazawa, et al., Efficient Synthesis of 2-Methoxy- and 4-Methoxy-Estrogens, J. Chem. Soc. Chem. Commun. (1983) p. 533-534.

Makoto Okada, et al., Efficient General Method for Sulfamoylation of a Hydroxyl Group, Tetrahedron Letters (2000) vol. 41, p. 7047-7051.

Philip C. Bulman Page., et al., Efficient Regioselective A-Ring Functionalization of Oestrogens, Tetrahedron (1990) vol. 46, No. 6, p. 2059-2068.

H. Peltoketo, et al., Complete Amino Acid Sequence of Human Placental 17β-Hydroxysteroid Dehydrogenase Deduced From cDNA, FEBS Letters (1988) vol. 239, No. 1, p. 73-77.

H. Peltoketo, et al., 17β-Hydroxysteroid Dehydrogenase (HSD)/17-Kesosteroid Reductase (KSR) Family; Nomenclature and Main Characteristics of the 17HSD/KSR Enzymes, Journal of Molecular Endocrinology (1999) vol. 23, p. 1-11.

Trevor M. Penning, et al., Molecular Endocrinology of Hydroxysteroid Dehydrogenases*, Endocrine Reviews (1997) vol. 18, No. 3, p. 281-305.

Atul Purohit, et al., The Effect of 2-Methoxyoestrone-3-O-Sulphamate on the Growth of Breast Cancer Cells and Induced Mammary Tumours, Int. J. Cancer (2000) vol. 85, p. 584-589.

Atul Purohit, et al., In Vivo Inhibition of Oestrone Sulphatase and Dehydroepiandrosterone Sulphatase by Oestrone-3-O-Sulphamate, Int. J. Cancer (1995) vol. 63, p. 106-111.

Atul Purohit, et al., Inactivation of Steroid Sulfatase by an Active Site-Directed Inhibitor, Estrone-3-O-Sulfamate, Biochemistry (1995) vol. 34, p. 11508-11514.

Atul Purohit, et al., In Vivo Activity of 4-Methylcoumarin-7-O-Sulfamate, A Nonsteroidal, Nonestrogenic Steroid Sulfatase Inhitbitor, Cancer Research (1996) vol. 56, p. 4950-4955.

Atul Purohit, et al., In Vivo Inhibition of Estrone Sulfatase Activity and Growth of Nitrosomethylurea-induced Mammary Tumors by 667 COUMATE[1], Cancer Research (2000) vol. 60, p. 3394-3396.

Atul Purohit, et al., Oestrogen Sulphatase Activity in Hormone-Dependent and Hormone-Independent Breast-Cancer Cells: Modulation by Steroidal and Non-Steroidal Therapeutic Agents, Int. J. Cancer (1992) vol. 50, p. 901-905.

Richard Poulin, et al., Stimulation of Cell Proliferation and Estrogenic Response by Adrenal $C_{19}$-$\Delta^5$-Steroids in the ZR-75-1 Human Breast Cancer Cell Line', Cancer Research (1986) vol. 46, p. 4933-4937.

Trevor J. Powles, Breast Cancer Prevention, Breast Cancer Res. (2000) vol. 2, p. 10-12.

Terhi Puranen, et al., Origin of Substrate Specificity of Human and Rat 17β-Hydroxysteroid Dehydrogenase Type 1, Using Chimeric Enzymes and Site Directed Substitutions, Endocrinology (1997) vol. 138, No. 8, p. 3532-3539.

L.W. Lawrence Woo, et al., Steroidal and Nonsteriodal Sulfamates As Potent Inhibitors of Steriod Sulfatase; Journal of Medical Chemistry (1998) vol. 41, p. 1068-1083.

Woo, et al., Active Site-Directed Inhibition of Steroid Sulphatase, Chemistry & Biology (2000) vol. 7, No. 10, 784-791.

L. W. Lawrence Woo, et al., Heteroatom-Substituted Analogues of the Active-Site Directed Inhibitor Estra-1,3,5 (10)-Trien-17-One-3-Sulphamate Inhibit Estrone Sulphatase by a Different Mechanism, J. Steroid Biochem. Molec. Biol. (1996) vol. 57, No. ½, p. 79-88.

Ling Wu, et al., Expression Cloning and Characterization of Human 17β-Hydroxysteroid Dehydrogenase Type 2, A Microsomal Enzyme Possessing 20α-Hydroxysteroid Dehydrogenase Activity, The Journal of Biological Chemistry (1993) vol. 268, No. 17, p. 12964-12969.

Pauline H. Yen, et al. Cloning and Expression of Steroid Sulfatase cDNA and the Frequent Occurrence of Deletions in STS Deficiency: Implications for X-Y Interchange, Cell (1987) vol. 49, p. 443-454.

Christina Stein, et al., Cloning and Expression of Human Steroid-Sulfatase, The Journal of Biological Chemistry (1989) vol. 264, No. 23, p. 13865-13872.

A.E. Wakeling, et al., Steroidal Pure Antioestrogens, Journal of Endocrinology (1987) vol. 112, p. R7-R10.

Gary J. Williams, et al., X-Ray Crystal Structure and Mechanism of Action of Oestrone 3-*O*-Sulphamate, A Synthetic Active Site-Directed Inhibitor of Oestrone Sulphatase, Pharmaceutical Sciences (1996) vol. 2, p. 11-16.

Martin R. Tremblay, et al., Overview of a Regional Approach to Design Type I 17β-Hydroxysteroid Dehydrogenase Inhibitors Without Estrognic Activity: Chemical Synthsis and Biological Evaluation, J. Steroid Biochem. Molec. Biol. (1998) vol. 66, No. 4, p. 179-191.

Martin R. Tremblay, et al., Synthesis of 16-(Bromoalkyl)-Estradiols Having Inhibitory Effect on Human Placental Estradiol 17β-Hydroxysteroid Dehydrogenase (17β-HSD Type 1), Bioorganic & Medicinal Chemistry (1995) Vol. 3, No. 5, p. 505-523.

Yushihiro Deyashiki, et al., Molecular Cloning and Characterization of Mouse Estradiol 17β-Dehydrogenase (A-Specific) A Member of the Aldoketoreductase Family, The Journal of Biological Chemistry (1995) vol. 270, No. 18, p. 10461-10467.

B.A. Miller, et al., Racial/Ethnic Patterns of Cancer in the United States, 1988-1992, National Cancer Institute (1996) Pub. No. 96-4104.

A. Purohit, et al., Non-Steroidal and Steroidal Sulfamates: New Drugs for Cancer Therapy, Molecular and Cellular Endocrinology (2001) vol. 171, p. 129-135.

Sabbir Ahmed, et al., Structure-Activity Relationship Study of Steroidal and Nonsteroidal Inhibitors of the Enzyme Estrone Sulfatase, Biochemical and Biophysical Research Communications (1999) vol. 254, p. 811-815.

S. Makela, et al. Inhibition of 17β-Hydroxysteroid Oxidoreductase by Flavonoids in Breast and Prostate Cancer Cells $_{(44237)}$, Proc. Soc. Exp. Biol. Med. (1998) vol. 217, p. 310-316.

Sigvard Kaae, Does Simple Mastectomy Followed by Irradiation Offer Survival Comparable to Radical Procedures? Int. J. Radiation Oncology Biol. Phys. (1997) vol. 2, p. 1163-1166.

B. Malini, et al., Inhibition of Steroid Sulphatase Activity by Tricyclic Coumarin Sulphamates, Journal of Steroid Biochemistry & Molecular Biology (2000) vol. 75, p. 253-258.

B. Matkovics, et al., Schmidt Reaction and Beckmann Rearrangement of Estrone and Its Derivatives, Acta Chim. Acad. Science Hungary (1974) vol. 80, p. 79-87.

W.R. Miller, Aromatase Inhibitors—Where Are They Now? British Journal of Cancer (1996) vol. 73, p. 415-417.

P. J. Nicholls, Breast Cancer Management: Science and Care Together, The Pharmaceutical Journal (1997) vol. 259, p. 459-470.

Bernard M. Regan, et al., 17- and 17a-Aza-D-Homosteroids, Journal of the American Chemical Society (1956) vol. 78, No. 3, p. 639-643.

N. Sakura, et al., Allergic Disease as an Association of Steroid Sulphatase Deficiency, J. Inherit. Metab. Dis. (1997) vol. 20, p. 807-810.

S. J. Santner, et al., In Situ Estrogen Production Via the Estrone Sulfatase Pathway in Breast Tumors: Relative Importance Versus the Aromatase Pathway, Journal of Clinical Endocrinology and Metabolism (1984) vol. 59, No. 1, p. 29-33.

C. M. Saunders, et al., Management of Early Breast Cancer, Oncol. In Pract. (1994)vol. 3, p. 4-8.

Michael J. Sexton, et al., Selective Estrogen Receptor Modulators: The Ideal Estrogen Replacement? Prim. Care. Update Ob/Gyns. (2001) vol. 8, No. 1, p. 25-30.

H. John Smith, et al., Inhibitors of Steroidogenesis As Agents for the Treatment of Hormone-Dependent Cancers, Exp. Opin. Ther. Patents (2001) vol. 11, No. 5, p. 789-824.

Early Breast Cancer Trialists Collaborative Group, Effects of Adjuvant Tamoxifen and of Cytotoxic Therapy on Mortality in Early Breast Cancer, NE Journal of Medicine (1988) vol. 310, No. 26, p. 1681-1692.

Coulson, Steroid Biosynthesis and Action, $2^{nd}$ Edition, Molecular mechanism of Drug Action (1994) p. 95-122.

S.X. Lin, et al., 3D-Structure of Human Estrogenic 17β-HSD1: Binding With Various Steroids, Journal of Steroid Biochemistry and Molecular Biology (1999) vol. 69, p. 425-429.

\* cited by examiner

STEROIDAL COMPOUNDS AS STEROID SULPHATASE INHIBITORS

INCORPORATION BY REFERENCE

This application is a continuation-in-part of International Patent Application PCT/GB2007/000686 filed Feb. 28, 2007 and published as WO 2007/099304 on Sep. 7, 2007, which claims priority from Great Britain Patent Application No. 0604142.0 filed Mar. 1, 2006.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

These and other embodiments are disclosed or are obvious from and encompassed by, the following Detailed Description.

FIELD OF INVENTION

The present invention relates to a compound. In particular the present invention provides compounds capable of inhibiting steroid sulphatase.

BACKGROUND TO THE INVENTION

Breast cancer is a devastating disease which remains to be a major cause of death for women in most Western countries. It is estimated to affect approximately 1 million women per year across the globe.[1]

Britain has one of the highest mortality rates for breast cancer in the world with over 35,000 women diagnosed each year accounting for nearly one in five of all cancer cases. It is estimated that 1 in 10 women living to the age of 85 in Britain will develop breast cancer during the course of her life. Although modern methods of treatment as well as an earlier detection of the disease have greatly improved survival rates, breast cancer remains the leading cause of death for women aged between 35-54.[2]

All women are at risk of breast cancer although a number of risk factors have been identified, most of them being related to women's hormonal and reproductive history as well as their family background of the disease. Women at higher risk are generally those with a strong family history of the disease, early onset of menarche, late onset of menopause or a first full-term pregnancy after the age of 30.[2]

In the earliest stages of a breast cancer, surgery appears to be the treatment of choice. In most of the cases, breast conserving surgical techniques, such as local incision of lump(s) in the breast(s), are involved rather than mastectomy. To prevent any recurrence of the disease, radiotherapy is often prescribed, particularly if breast conserving techniques have been involved.[3] It is also used to reduce large tumours to an operable size so that conservational surgery can be carried out.[4]

For advanced breast cancers, when the tumour has spread or recurred, the aim in the treatment is no longer to cure but to reach a palliative control. This is the case when metastases of the tumour have reached locations such as bones, skin, lymph, node or brain. The treatment varies depending on the hormonal status of the patient (whether it is a pre- or post-menopausal woman to be treated) and depending on the type of tumour. Certain tumours have indeed been proven to rely on estrogens for their growth and development, leading to what is called a Hormone Dependent Breast Cancer (HDBC, see I-1). While non HDBC are treated with chemotherapy, where the aim is to kill differentially tumour cells using a combination of cytotoxic agents,[5] HDBC are expected to respond to endocrine therapy.

The concept of hormone dependent tumours appeared in the early 1960s, when the model of estrogens action was first introduced.[6] In order for estrogens to regulate cell growth and function in humans, a specific protein, called the human Oestrogen Receptor (hER), must be present.[7] This protein, localised in the nucleus, interacts with estrogens resulting in the formation of a binding complex. This acts as a transcription factor by activating production of m-RNA from specific genes, one or more of which are probably essential for efficient tumour cell growth.

Patients with a measurable level of receptor protein are classified as oestrogen-receptor-positive (ER+) with opposition to oestrogen-receptor-negative (ER−). About 50% of pre-menopausal women and 75% of post-menopausal women fall into the ER+ group[8] where the development of breast cancers can be directly linked to the presence of estrogens. Endocrine therapy, where the use of drugs results in a deprivation of estrogenic stimulation to cells, has proven to be an effective approach to the treatment of HDBC. Originally, two classes of drugs, responding to different strategies, were developed: anti-oestrogens and aromatase inhibitors.

Anti-oestrogens, as antagonists of the oestrogen receptor, have been one of the first treatments considered for HDBC. Their action relies on their ability to bind competitively to the specific receptor protein hER, thus preventing access of endogenous estrogens to their specific binding site. Consequently, the natural hormone is unable to maintain tumour growth.

Of the anti-oestrogens commonly used in breast cancer therapy, tamoxifen (below) is the most widely used because of the very low toxicity profile of the molecule. Despite its non-steroidal skeleton, tamoxifen possesses a mixed agonist-antagonist activity that limits its therapeutic potential.[9] In addition, some form of drug resistance has been reported in patients after long-term tamoxifen treatment.[10]

Novel pure anti-oestrogenic drugs, such as ICI 164384 (below), have since been discovered but the loss of potency compared with that of tamoxifen suggested the need to design more highly potent targets.[11]

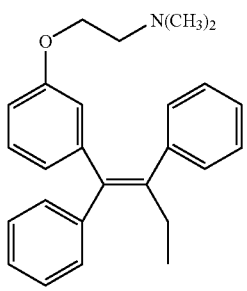

Tamoxifen

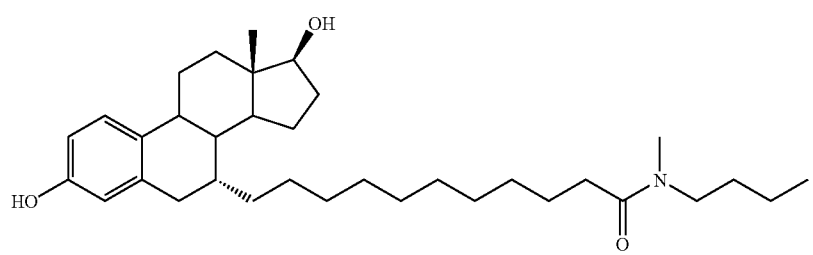

ICI 164384

For some years now, a new type of anti-oestrogen has emerged, combining oestrogen agonism on target tissues such as bone or liver and antagonism and/or minimal agonism in reproductive tissues such as breasts or uterus.[12] These compounds, designed as Selective Oestrogen Receptor Modulators (SERMs), are not only potentially effective in reducing a patient's risk of breast carcinoma but they have also been shown to increase bone mineral density and prevent osteoporosis in post-menopausal women. Raloxifen is the first of this class of compounds to be used clinically.[13] More SERMs are currently in clinical trials and these molecules might one day replace tamoxifen as the first line treatment for women with HDBC.

The use of therapeutic agents that inhibit one or several enzyme of the steroid biosynthesis pathway represents another important strategy to control of the development of oestrogen-dependent tumours.[14] The enzyme aromatase, which converts androgenic C19 steroids to estrogenic C18 steroids, has been the prime target for reducing oestrogen levels. This enzyme complex, which contains a cytochrome P450 haemoprotein, catalyses the aromatisation of the androgen A-ring with the subsequent loss of the C19 methyl group to yield estrogens.

Aminoglutethimide (below) was the first aromatase inhibitor used for the treatment of breast cancer. It however showed a number of undesirable side effects given its wide spectrum of inhibitory effects on other P450-dependant enzymes, and attempts to improve on the original structure have led to a number of non-steroidal compounds entering clinical trials.[15] The last generation developed compounds such as letrozole, which combine high potency and high selectivity for the enzyme, and are also better tolerated.

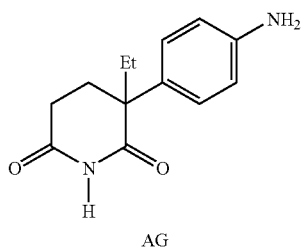

AG

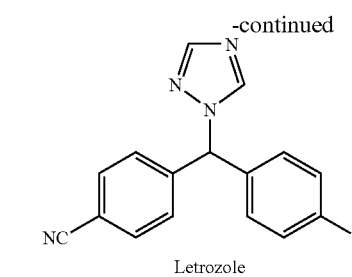

Letrozole

Structure of different types of aromatase inhibitors. Generation I: aminoglutethimide, AG; generation III, letrozole.

Traditionally, aromatase inhibitors are reserved as second line treatment for advanced HDBC patients whose diseases are no longer controlled by tamoxifen. However, because of the extreme good toxicity profile of some of the latest aromatase inhibitors, recent clinical trials have been conducted to assess their suitability as first line treatment for HDBC.

Strong evidence has emerged over the past decade, both biochemically and clinically, that the sole inhibition of the enzyme aromatase cannot afford an effective reduction of estrogenic stimulation to HDBC, the reason being that other pathways are involved in oestrogen biosynthesis. The sulphatase pathway is now considered to be the major route for breast tumour oestrogen synthesis since sulphatase activity was found to provide 10 fold more oestrone than the aromatase activity.[16]

In the sulphatase pathway, estrogens are synthesised from the highly available precursor oestrone-sulphate, via two enzymes (scheme below): oestrone sulphatase (STS) which hydrolyses oestrone-sulphate into oestrone, and 17β-hydroxysteroid dehydrogenase (17β-HSD) which reduces oestrone into oestradiol. These two enzymes represent the latest targets for oestrogen deprivation strategies.

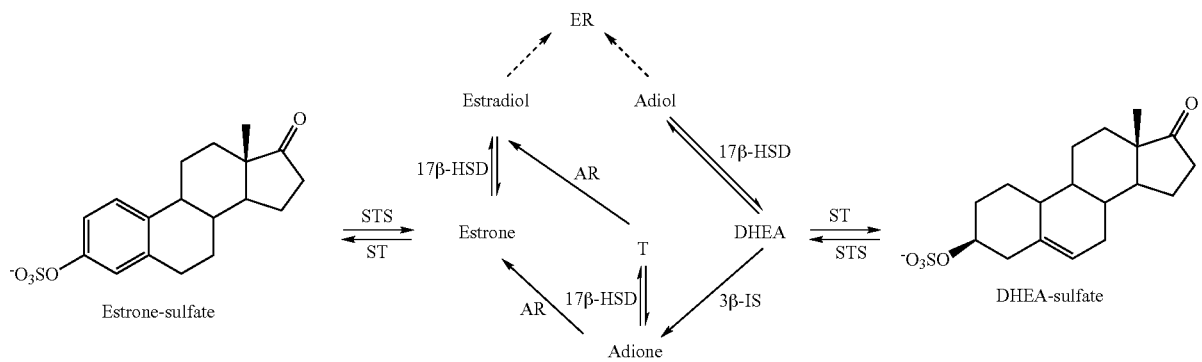

Origin of estrogens in normal and tumoral breast cells. AR, aromatase; ST: steroid sulfotransferase; STS, steroid sulphatase; 17β-HSD, 17β-hydroxysteroid dehydrogenase; 3β-IS, 3β-hydroxysteroid dehydrogenase $\Delta^5,\Delta^4$-isomerase; ER, oestrogen receptor.

Several potent inhibitors have been identified for oestrone sulphatase. They all share the common structural feature of an aromatic ring bearing a substituent that mimics the phenolic A-ring of the enzyme substrate, oestrone-sulphate. On the development of steroidal inhibitors, a wide variety of chemical groups have been introduced at C3, of which the 3-O-sulfamate was found to be the most potent for the oestrone molecule. The resulting compound, estrone-3-O-sulfamate (below) led to the identification of the aryl-O-sulphamate structure as an active pharmacophore required for potent inhibition of STS. EMATE was shown to inhibit steroid sulphatase activity in a time- and concentration-dependent manner[17] and was active in vivo on oral administration.[18] It was however revealed to be highly estrogenic which raised the need to design STS inhibitors devoid of agonist activity on hER.

To avoid the problems linked to an active steroid nucleus, non steroid-based inhibitors have been synthesised. Coumarin sulphamate such as 4-methylcoumarin-7-O-sulfamate (COUMATE, below), where the active pharmacophore is conserved, have been among the first inhibitors of that type to be identified.[19] Although COUMATE is less potent than EMATE, it has the advantage of being non estrogenic.[20] Some tricyclic coumarin-based sulphamates have also been developed and turned out to be much more potent than COUMATE, while retaining its non estrogenic characteristic.[21] 667COUMATE, which is some 3 times more potent than EMATE in vitro is now in pre-clinical development for clinical trials.[22]

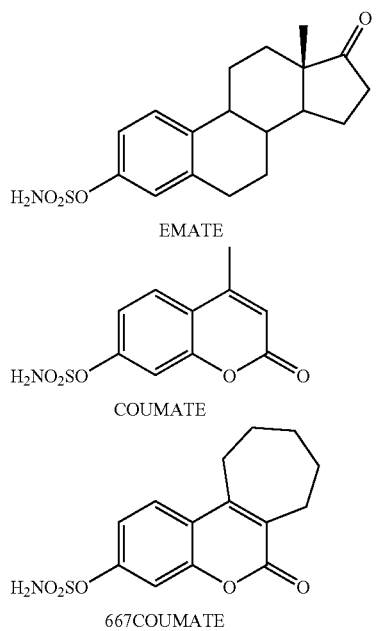

Structures of the steroid sulphatase inhibitors EMATE, COUMATE and 667COUMATE.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (EMATE). It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS may have been attained in EMATE, it is possible that oestrone may be released during sulphatase inhibition and that EMATE and its oestradiol congener may possess oestrogenic activity.

17β-HSD, which catalyses the final step in estrogens and androgens biosynthesis, also appeared as a target for oestrogen deprivation strategies. This enzyme is responsible for the interconversion of the oxidised form (less active) and the reduced form (more active) of steroids. Its activity directly supports the growth and development of oestrogen dependent tumours since it preferably reduces oestrone into estradiol[25] and in a minor extend, via the conversion of the androgen DHEA into androstenediol (Adiol), which has recently been proven to have estrogenic properties and to be able to bind to the oestrogen receptor.[26]

17β-HSD belongs to a family of isoenzymes, 11 of which have been so far identified and cloned.[27] Each type has a selective substrate affinity and directional activity which means that selectivity of drug action has to be achieved. 17β-HSD type 1 is the isotype that catalyses the interconversion of oestrone and oestradiol.

Unlike STS inhibitors, only few 17β-HSD inhibitors have been reported. Most of the steroidal inhibitors for 17β-HSD type 1 have in common a D-ring modified structure. Oestradiol derivatives which contain a side-chain with a good leaving group at the 16α-position have been shown to be a potent class of inhibitors. In particular, 16α-(bromoalkyl)-estradiol[28] where the side-chains exhibit high reactivity towards nucleophilic amino-acids residues in the active site of the enzyme were found to be promising irreversible inhibitors. Analogues containing short bromoalkyl moieties at position 16 exhibited the highest activity with 16α-(Bromopropyl)-oestradiol, followed by 16α-(Bromobutyl)-oestradiol, the most potent of the series (3 and 4). They, however, turned out to be pure agonists of the oestrogen receptor.

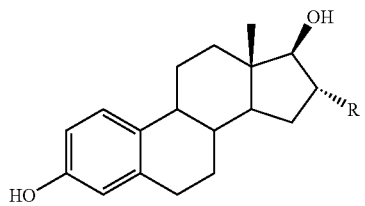

3 R = $(CH_2)_3Br$
4 R = $(CH_2)_4Br$

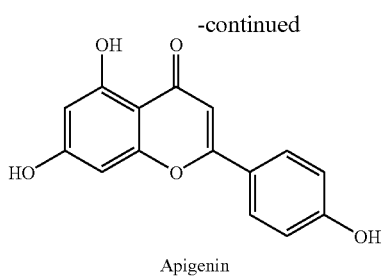

Apigenin

17β-HSD type 1 inhibitors: 16α-(bromopropyl)-oestradiol, 3;

16α-(bromopropyl)-oestradiol, 4 and a flavone derivative, apigenin.

In an attempt to eliminate the intrinsic oestrogenicity of potent inhibitors and possibly at the same time engineer anti-oestrogenic properties into the molecule, several 16α-(broadly)-oestradiol derivatives bearing the C7α-alkylamide side chain of the known anti-oestrogen ICI 164384 were synthesised.[29] However, rather poor inhibition of 17β-HSD type 1 was obtained, with estrogenic and anti-oestrogenic properties not completely abolished or introduced respectively.

In parallel, non-steroidal inhibitors of 17β-HSD type 1 have been designed. Flavonoids, which are structurally similar to estrogens, are able to bind to the oestrogen receptor with estrogenic or anti-estrogenic activities.[30] Their action on aromatase activity is well documented and in recent studies, they were found to reduce the conversion of oestrone into oestradiol catalysed by 17β-HSD type 1.[31] Flavone derivatives, such as apigenin (FIG. 6) emerged from a SAR study as a promising compounds with some inhibitory activity on 17β-HSD type 1 without being estrogenic at the inhibitory concentration.[32]

Ahmed et al (Biochem Biophys Res Commun 1999 Jan. 27; 254 (3): 811-5) report on a structure-activity relationship study of steroidal and nonsteroidal inhibitors of STS.

Steroid dehydrogenases (DH) such as oestradiol 17β-hydroxysteroid dehydrogenases (E2HSD) have pivotal roles in regulating the availability of ligands to interact with the oestrogen receptor. E2HSD Type I reduces oestrone (E1) to the biologically active oestrogen, oestradiol (E2), while E2HSD Type II inactivates E2 by catalysing its oxidation to E1. Thus the identification of compounds having DH inhibitory activity, in particular, inhibitors of E2HSD Type I, could be of therapeutic value in inhibiting the formation of E2.

WO03/033518 discloses compounds of the formula

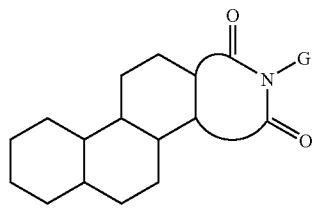

wherein G is H or a substituent. The compounds have activity as inter alia steroid sulphatase inhibitors.

SUMMARY ASPECTS OF THE PRESENT INVENTION

The present invention provides novel compounds which are capable of acting as effective steroid sulphatase inhibitors.

The present invention identifies that the compounds of the present application are effective steroid sulphatase inhibitors.

FIG. 1 shows some of the enzymes involved in the in situ synthesis of oestrone from oestrone sulphate, and oestradiol. "STS" denotes Oestrone Sulphatase, "E2DH Type I" denotes Oestradiol 17β-hydroxysteroid dehydrogenase Type I or Oestradiol 17β-hydroxysteroid dehydrogenase Type 1, 3, 5 and/or 7 and "E2DH Type II" denotes Oestradiol 17β-hydroxysteroid dehydrogenase Type II or Oestradiol 17β-hydroxysteroid dehydrogenase Type 2 and/or 8.

As can be seen, two enzymes that are involved in the peripheral synthesis of oestrogens are the enzyme Oestradiol 17β-hydroxysteroid dehydrogenase and the enzyme oestrone sulphatase.

In situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Thus, there is an urgent need to develop new therapies for the treatment of these cancers.

The present invention therefore seeks to overcome one or more of the problems associated with the prior art methods of treating breast and endometrial cancers.

In one aspect, therefore, the present invention provides a use of a compound for the preparation of a medicament that can affect, such as substantially inhibit, the oestrone sulphatase pathway—which pathway converts oestrone to and from oestradiol—and/or affect, such as substantially inhibit, the steroid dehydrogenase pathway—which pathway converts oestrone to and from oestradiol.

This aspect of the present invention is advantageous because by the administration of one type of compound it is possible to block the synthesis of oestradiol from oestrone or E1S. Hence, the present invention provides compounds that have considerable therapeutic advantages, particularly for treating breast and endometrial cancers.

The compounds of the present invention may comprise other substituents. These other substituents may, for example, further increase the activity of the compounds of the present invention and/or increase stability (ex vivo and/or in vivo).

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

DETAILED ASPECTS OF THE PRESENT INVENTION

Figure 1:
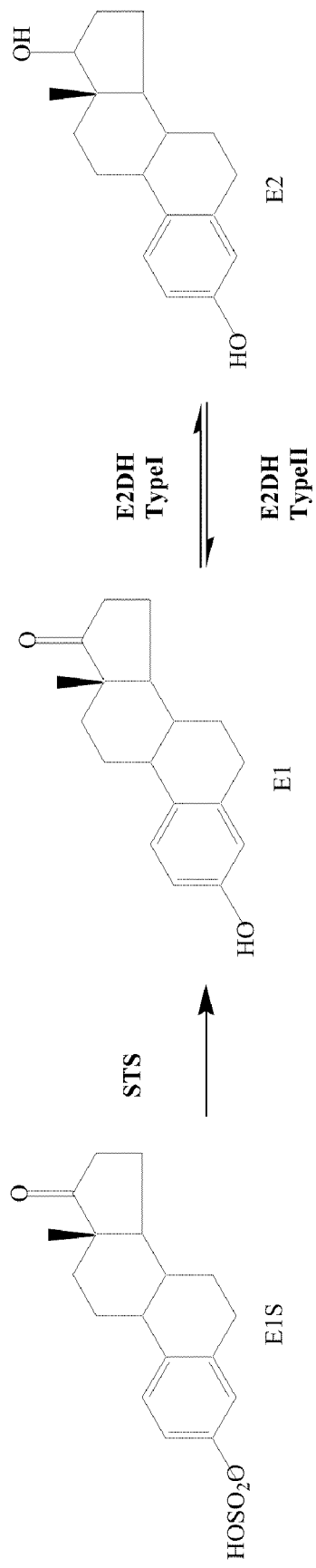
FIG. 1 shows some of the enzymes involved in the in situ synthesis of oestrone from oestrone sulphate, and oestradiol. "STS" denotes Oestrone Sulphatase, "E2DH Type I" denotes Oestradiol 17β-hydroxysteroid dehydrogenase Type I or Oestradiol 17β-hydroxysteroid dehydrogenase Type 1, 3, 5 and/or 7 and "E2DH Type II" denotes Oestradiol 17β-hydroxysteroid dehydrogenase Type II or Oestradiol 17β-hydroxysteroid dehydrogenase Type 2 and/or 8.

According to one aspect of the present invention, there is provided a compound having Formula I

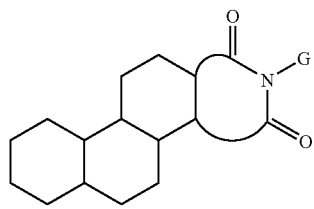

Formula I wherein G is a fluorocarbyl group.

According to one aspect of the present invention, there is provided a pharmaceutical composition comprising a compound having Formula I

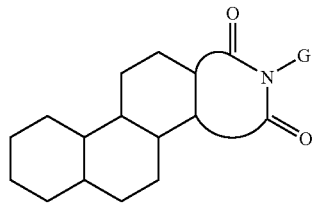

Formula I wherein G is a fluorocarbyl group, admixed with a pharmaceutically acceptable carrier, diluent, excipient or adjuvant.

According to one aspect of the present invention, there is provided a compound having Formula I

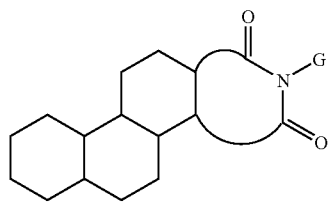

Formula I wherein G is a fluorocarbyl group, for use in medicine.

According to one aspect of the present invention, there is provided use of a compound a compound having Formula I

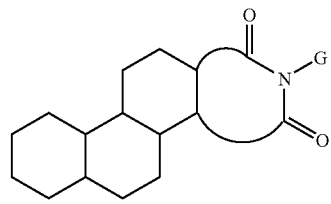

Formula I wherein G is a fluorocarbyl group, in the manufacture of a medicament for use in the therapy of a condition or disease associated with steroid sulphatase (STS).

According to one aspect of the present invention, there is provided use of a compound having Formula I

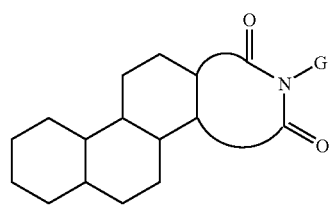

Formula I wherein G is a fluorocarbyl group, in the manufacture of a medicament for use in the therapy of a condition or disease associated with adverse STS levels.

According to one aspect of the present invention, there is provided use of a compound having Formula I

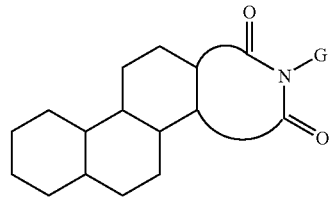

Formula I wherein G is a fluorocarbyl group, in the manufacture of a pharmaceutical for inhibiting steroid sulphatase (STS) activity.

According to one aspect of the present invention, there is provided a method of inhibiting steroid sulphatase (STS) activity in a subject in need of same, the method comprising administering a compound a compound having Formula I

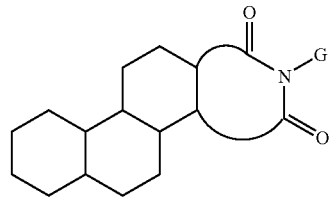

Formula I wherein G is a fluorocarbyl group.

According to one aspect of the present invention, there is provided use of a compound having Formula I

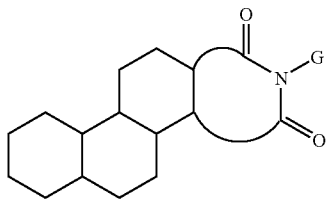

Formula I wherein G is a fluorocarbyl group, in the manufacture of a pharmaceutical for modulating and/or arresting and/or inhibiting cell cycling and/or for modulating and/or inducing apoptosis.

For ease of reference, these and further aspects of the present invention are now discussed under appropriate section headings. However, the teachings under each section are not necessarily limited to each particular section.

Preferable Aspects
Ring System

In some aspects of the present invention, preferably the compound has Formula II

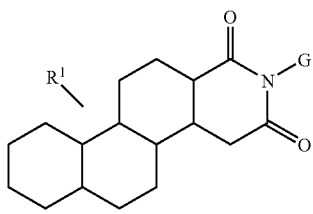

Formula II wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula III

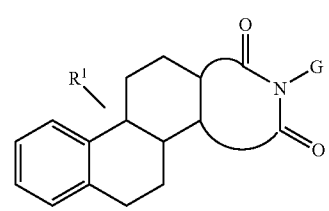

Formula III wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula IV

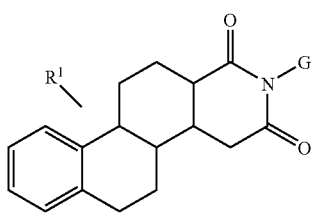

Formula IV wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula V

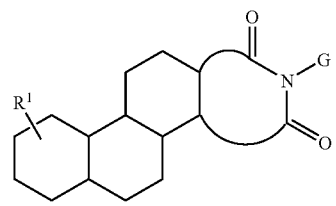

Formula V wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula VI

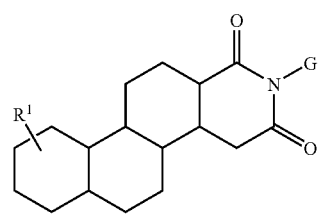

Formula VI wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula VII

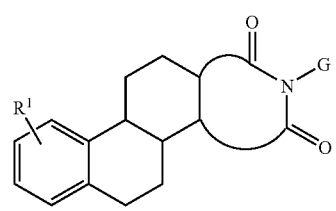

Formula VII wherein G is a fluorocarbyl group, and wherein $R^1$ is any one of —OH, a sulphamate group, a phosphonate group, a thiophosphonate group, a sulphonate group or a sulphonamide group.

In some aspects of the present invention, preferably the compound has Formula VIII Formula VIII

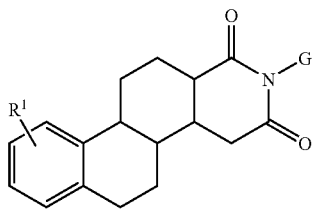

wherein G is a fluorocarbyl group, and wherein R¹ is any one of —OH, a sulphamate group, a phosphonate group, a thiophosphonate group, a sulphonate group or a sulphonamide group.

In some aspects of the present invention, preferably the compound has Formula IX Formula IX

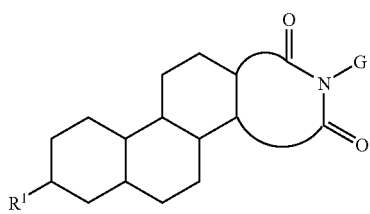

wherein G is a fluorocarbyl group, and wherein R¹ is any one of —OH, a sulphamate group, a phosphonate group, a thiophosphonate group, a sulphonate group or a sulphonamide group.

In some aspects of the present invention, preferably the compound has Formula X

Formula X

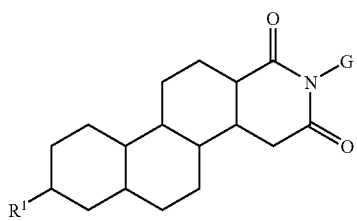

wherein G is a fluorocarbyl group, and wherein R¹ is any one of —OH, a sulphamate group, a phosphonate group, a thiophosphonate group, a sulphonate group or a sulphonamide group.

In some aspects of the present invention, preferably the compound has Formula XI Formula XI

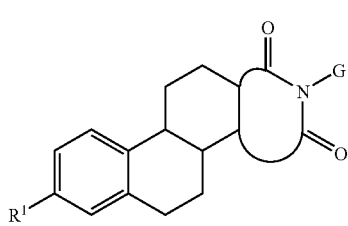

wherein G is a fluorocarbyl group, and wherein R¹ is any one of —OH, a sulphamate group, a phosphonate group, a thiophosphonate group, a sulphonate group or a sulphonamide group.

In some aspects of the present invention, preferably the compound has Formula XII Formula XII

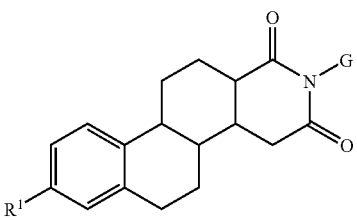

wherein G is a fluorocarbyl group, and wherein R¹ is any one of —OH, a sulphamate group, a phosphonate group, a thiophosphonate group, a sulphonate group or a sulphonamide group.

In some aspects of the present invention, preferably the compound has Formula XIII Formula XIII

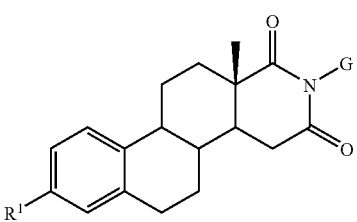

wherein G is a fluorocarbyl group, and wherein R¹ is any one of —OH, a sulphamate group, a phosphonate group, a thiophosphonate group, a sulphonate group or a sulphonamide group.

A very highly preferred compound has the formula

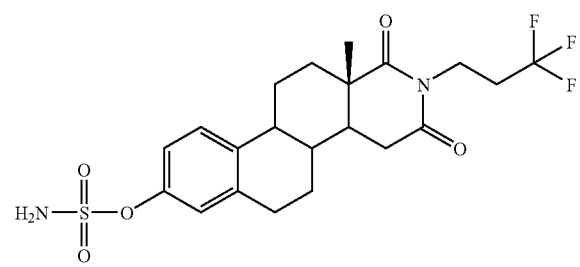

or a pharmaceutically acceptable salt or ester form thereof.

As it is well known in the art, a classical steroidal ring structure has the generic formula of:

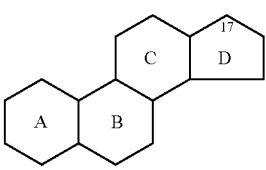

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere has steroidal properties.

In this regard, the ring system of the present invention is analogous to a steroidal ring structure and may be a bio-isostere of a steroidal ring structure.

The structure of a present polycyclic structure can be presented as:

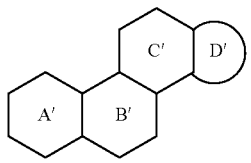

wherein each ring A', B', and C' independently represents a heterocyclic ring or a non-heterocyclic ring, and wherein each ring may be independently substituted or unsubstituted, saturated or unsaturated.

By way of example, any one or more of rings A', B', C' and D' may be independently substituted with suitable groups—such as an alkyl group, an aryl group, a hydroxy group, a halo group, a hydrocarbyl group, an oxyhydrocarbyl group etc.

At least one of A', B', and C' may be a heterocyclic group (a heterocycle) or a non-heterocyclic group.

At least one of A', B', C' and D' may be a saturated ring structure or an unsaturated ring structure (such as an aryl group).

Preferably, at least one of A', B', C' and D' is an aryl ring.

Preferably the compound will contain, inclusive of all substituents, no more than 50 about carbon atoms, more usually no more than about 30 to 40 carbon atoms.

An example of D' is a five or six membered ring.

Preferred steroidal nuclei rings A'-D' on which the compounds of the present invention may be based include rings A-D of:

Oestrones and Substituted Oestrones, Viz:

| oestrone | 16β-OH-oestrone |
|---|---|
| 4-OH-oestrone | 17-deoxyoestrone |
| 6α-OH-oestrone | 2-OH-oestrone |
| 7α-OH-oestrone | 2-MeO-oestrone |
| 16α-OH-oestrone | oestrone |

Oestradiols and Substituted Oestradiols, Viz:

| 4-OH-17β-oestradiol | 16β-OH-17β-oestradiol |
|---|---|
| 6α-OH-17β-oestradiol | 17α-oestradiol |
| 7α-OH-17β-oestradiol | 17β-oestradiol |
| 4-OH-17α-oestradiol | 17α-ethinyl-17β-oestradiol |
| 6α-OH-17α-oestradiol | 17β-ethinyl-17α-oestradiol |
| 7α-OH-17α-oestradiol | 17-deoxyoestradiol |
| 16α-OH-17α-oestradiol | 2-OH-17α-oestradiol |
| 16α-OH-17β-oestradiol | 2-OH-17β-oestradiol |
| 16β-OH-17α-oestradiol | 2-MeO-17α-oestradiol |
| | 2-MeO-17β-oestradiol |

Oestriols and Substituted Oestriols, Viz:

| oestriol | 17-deoxyoestriol |
|---|---|
| 4-OH-oestriol | 2-OH-oestriol |
| 6α-OH-oestriol | 2-MeO-oestriol |
| 7α-OH-oestriol | |

Dehydroepiandrosterones and Substituted Dehydroepiandrosterones, Viz:

| dehydroepiandrosterones | 16α-OH-dehydroepiandrosterone |
|---|---|
| 6α-OH-dehydroepiandrosterone | 16β-OH-dehydroepiandrosterone |
| 7α-OH-dehydroepiandrosterone | 5-androstenediol |

Group G

Group G is a fluorocarbyl group. The term "fluorocarbyl", as used herein, means a group comprising at least carbon and fluorine atoms.

In one embodiment, group G is a perfluoroalkyl group. More preferably, group G is a C1-10 perfluoroalkyl group.

The term "perfluoroalkyl" as used herein refers to an alkyl group wherein all of the hydrogen atoms have been replaced with fluorine. Examples of perfluoroalkyl groups are trifluoromethyl, pentafluoroethyl, heptafluoropropyl etc.

In an alternative preferred embodiment, group G comprises at least carbon, fluorine and one further element. More preferably, group G comprises at least carbon, fluorine and hydrogen. More preferably, group G comprises only carbon, fluorine and hydrogen.

Preferably, group G comprises from 1 to 10 carbon atoms, more preferably from 1 to 6, more preferably from 1 to 3.

Preferably, group G has the formula -A-B, wherein A is a straight, branched or cyclic alkylene group of 1 to 9 carbon atoms, and B is a straight, branched or cyclic perfluoroalkyl group of from 1 to 10 carbon atoms. Preferably, A is a group of the formula —$(CH_2)_n$— wherein n is an integer from 1 to 9. Preferably, A has two carbon atoms. Preferably, B is a group of the formula —$(CF_2)_m CF_3$ wherein m is 0 or an integer of from 1 to 9. Preferably, B has one carbon atom.

Preferably, group G has the formula —$(CH_2)_n(CF_2)_m CF_3$ wherein n is an integer from 1 to 9, m is 0 or an integer from 1 to 9. Preferably, n+m is between 1 and 10. Preferably, n is 2. Preferably, m is 0.

Most preferably, group G is 3,3,3-trifluoropropyl (—$CH_2CH_2CF_3$).

$R^1$ Group

Group $R^1$ of the compounds of the present invention is any one of —OH, a sulphamate group, a phosphonate group, a thiophosphonate group, a sulphonate group or a sulphonamide group.

In one preferred aspect $R^1$ is preferably a sulphamate group.

$R^1$ or the sulphamate group may be a sulphamate group of the formula

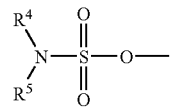

wherein $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

In an alternative preferred embodiment, $R^1$ is —OH.

In some aspects of the present invention, preferably at least one of $R^4$ and $R^5$ is H.

In some aspects of the present invention, preferably $R^4$ and $R^5$ are H.

Substituents

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. The ring system may contain one or more degrees of unsaturation, for example is some aspects one or more rings of the ring system is aromatic. The ring system may be carbocyclic or may contain one or more hetero atoms.

The compound of the invention, in particular the ring system compound of the invention of the present invention may contain substituents other than those show herein. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

In general terms the ring system A'B'C'D' of the present compounds may contain a variety of non-interfering substituents. In particular, the ring system A'B'C'D' may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

For some compounds of the present invention, it is preferred that the ring system is substituted with a hydrocarbylsulphanyl group. More preferably the A' ring of the ring system is substituted with a hydrocarbylsulphanyl group. The term "hydrocarbylsulphanyl" means a group that comprises at least hydrocarbyl group (as herein defined) and sulphur, preferably —S-hydrocarbyl, more preferably —S-hydrocarbon. That sulphur group may be optionally oxidised.

For some compounds of the present invention, it is highly preferred that at least the 2 position of the A' ring of the ring system is substituted with a hydrocarbylsulphanyl group.

Preferably the hydrocarbylsulphanyl group is —S—$C_{1-10}$ alkyl, more preferably —S—$C_{1-5}$ alkyl, more preferably —S—$C_{1-3}$ alkyl, more preferably —S—$CH_2CH_2CH_3$, —S—$CH_2CH_3$ or —$SCH_3$ For some compounds of the present invention, it is highly preferred that the A' ring of the ring system is substituted with an alkoxy group.

For some compounds of the present invention, it is highly preferred that at least the 2 position of the A' ring of the ring system is substituted with an alkoxy group.

Preferably the alkoxy group is methoxy.

For some compounds of the present invention, it is highly preferred that at least the A' ring of the ring system is substituted with an hydrocarbyl group.

For some compounds of the present invention, it is highly preferred that at least the 2 position of the A' ring of the ring system is substituted with an alkyl group.

Preferably the alkyl group is ethyl.

For some compounds of the present invention, it is highly preferred that the compound comprises at least two or more of sulphamate group, a phosphonate group, a thiophosphonate group, a sulphonate group or a sulphonamide group.

For some compounds of the present invention, it is highly preferred that the compound comprises at least two sulphamate groups.

For some compounds of the present invention, it is highly preferred that the compound comprises at least two sulphamate groups, wherein said sulphamate groups are not on the same ring.

For some compounds of the present invention, it is highly preferred that the A' ring of the ring system comprises at least one sulphamate group and wherein the D' ring of the ring system comprises at least one sulphamate group.

In some aspects of the present invention, preferably the A' ring contain one or more of an alkoxy substituent and an alkyl substituent. Thus according to one aspect of the present invention, there is provided a compound having Formula XIII

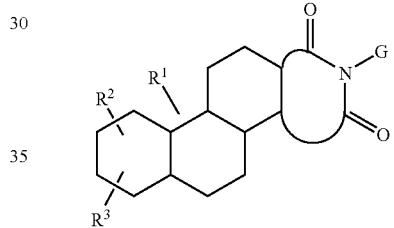

Formula XIII wherein $R^2$ and $R^3$ are independently selected from H and hydrocarbyl groups, wherein at least one of $R^2$ and $R^3$ is a hydrocarbyl group.

In preferred aspects of the present invention, there is provided a compound selected from compounds having Formula XIV to XIX

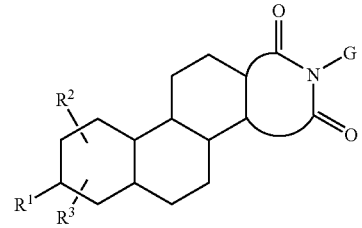

Formula XIV

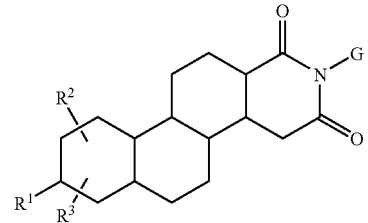

Formula XV

-continued

Formula XVI

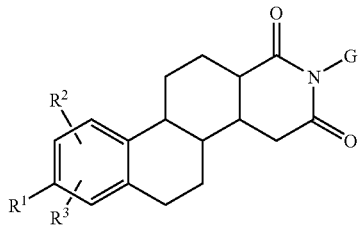

Formula XVII

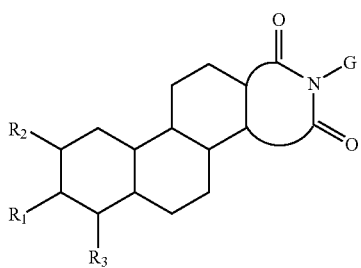

Formula XVIII

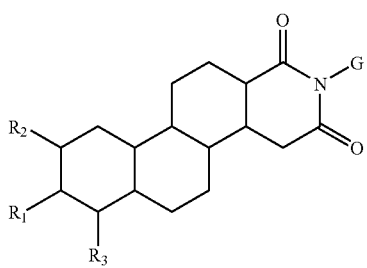

Formula XIX

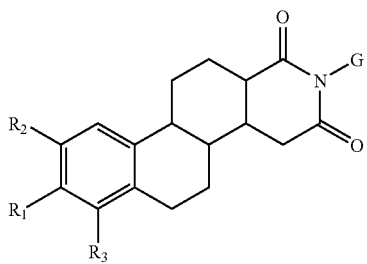

wherein $R^2$ and $R^3$ are independently selected from H and hydrocarbyl groups, wherein at least one of $R^2$ and $R^3$ is a hydrocarbyl group.

Preferably at least one of $R^2$ and $R^3$ is an alkyl group. Preferably at least one of $R^2$ and $R^3$ is $C_1$-$C_{10}$ alkyl group, preferably $C_1$-$C_6$ alkyl group, preferably $C_1$-$C_3$ alkyl group. Preferably at least one of $R^2$ and $R^3$ is —$CH_3$ or —$CH_2CH_3$.

In one aspect preferably $R^2$ is a hydrocarbyl group and $R^3$ is H.

In another preferred aspect, at least one of $R^2$ and $R^3$ is an alkoxy group. Preferably at least one of $R^2$ and $R^3$ is methoxy.

Highly preferred compounds of the present invention may be selected from

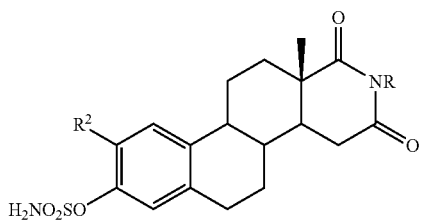

wherein
$R=(CH_2)_2CF_3$ and $R_2=H$
$R_2=OMe$
$R_2=$—S-Me

Further Aspects

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS According to one aspect of the present invention, there is provided the use of a compound according to the present invention in the manufacture of a medicament for use in the therapy of a condition or disease associated with adverse STS levels.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The compounds of the present invention may be in the form of a salt.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

We have also identified that in some aspects of the present invention the present compounds may also inhibit the activity of steroid dehydrogenase (HSD).

By steroid dehydrogenase or HSD it is meant 17β hydroxy steroid dehydrogenase. In one aspect the 17β hydroxy steroid dehydrogenase is EC 1.1.1.62

Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

Thus in further aspects the present invention provides
Use of a compound of the present invention in the manufacture of a medicament for use in the therapy of a condition or disease associated with steroid dehydrogenase.
Use of a compound of the present invention in the manufacture of a medicament for use in the therapy of a condition or disease associated with adverse steroid dehydrogenase levels.
Use of a compound of the present invention in the manufacture of a pharmaceutical for inhibiting steroid dehydrogenase activity.

Use of a compound of the present invention in the manufacture of a pharmaceutical for inhibiting steroid dehydrogenase activity.

A method comprising (a) performing a steroid dehydrogenase assay with one or more candidate compounds of the present invention; (b) determining whether one or more of said candidate compounds is/are capable of modulating steroid dehydrogenase activity; and (c) selecting one or more of said candidate compounds that is/are capable of modulating steroid dehydrogenase activity.

A method comprising (a) performing a steroid dehydrogenase assay with one or more candidate compounds of the present invention; (b) determining whether one or more of said candidate compounds is/are capable of inhibiting steroid dehydrogenase activity; and (c) selecting one or more of said candidate compounds that is/are capable of inhibiting steroid dehydrogenase activity.

A compound identified by the above methods, their use in medicine and pharmaceutical composition comprising the compounds optionally admixed with a pharmaceutically acceptable carrier, diluent, excipient or adjuvant.

In some aspects of the present invention, it is preferred that the steroid dehydrogenase is steroid dehydrogenase Type I.

In some aspects of the present invention, it is preferred that the steroid dehydrogenase is steroid dehydrogenase Type II Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

We have also identified that in some aspects it is not necessary for the compounds of the present invention to be substituted with one of a sulphamate group, a phosphonate group, a thiophosphonate group, a sulphonate group or a sulphonamide group, to inhibit the activity of steroid dehydrogenase (HSD). Thus in some aspects the present invention provides a compound as defined herein wherein R1 is any substituent. In this aspect preferably R1 is H, OH or a hydrocarbyl group, more preferably OH.

Thus in further aspects the present invention provides a compound having the formula

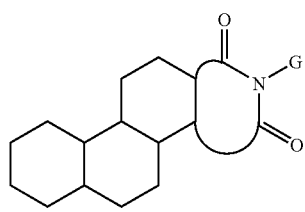

wherein G is a fluorocarbyl group,

Use of the compound in the manufacture of a medicament for use in the therapy of a condition or disease associated with steroid dehydrogenase.

Use of the compound in the manufacture of a medicament for use in the therapy of a condition or disease associated with adverse steroid dehydrogenase levels.

Use of the compound in the manufacture of a pharmaceutical for inhibiting steroid dehydrogenase activity.

Use of the compound in the manufacture of a pharmaceutical for inhibiting steroid dehydrogenase activity.

A method comprising (a) performing a steroid dehydrogenase assay with one or more candidate compounds having the above formula; (b) determining whether one or more of said candidate compounds is/are capable of modulating steroid dehydrogenase activity; and (c) selecting one or more of said candidate compounds that is/are capable of modulating steroid dehydrogenase activity.

A method comprising (a) performing a steroid dehydrogenase assay with one or more candidate compounds having the above formula; (b) determining whether one or more of said candidate compounds is/are capable of inhibiting steroid dehydrogenase activity; and (c) selecting one or more of said candidate compounds that is/are capable of inhibiting steroid dehydrogenase activity.

A compound identified by the above methods, their use in medicine and pharmaceutical composition comprising the compounds optionally admixed with a pharmaceutically acceptable carrier, diluent, excipient or adjuvant.

Some Advantages

One key advantage of the present invention is that the compounds of the present invention can act as STS inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity.

Another advantage is that some of the compounds may not be capable of being metabolised to compounds which display or induce hormonal activity.

Some of the compounds of the present invention are also advantageous in that they may be orally active.

Some of the compounds of the invention have an improved duration of action in vivo compared with known STS inhibitors.

Some of the compounds of the present invention may useful for the treatment of cancer, such as breast cancer, as well as (or in the alternative) non-malignant conditions, such as the prevention of auto-immune diseases, particularly when pharmaceuticals may need to be administered from an early age.

Thus, some of the compounds of the present invention are also believed to have therapeutic uses other than for the treatment of endocrine-dependent cancers, such as the treatment of autoimmune diseases.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454 (1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20 (6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet. 1999 Mar.; 29 (2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact MCF-7 breast cancer cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200μ molar, preferably less than 150μ molar, preferably less than 100μ molar, preferably less than 75μ molar, preferably less than 50μmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS activity.

Steroid Dehydrogenase

Steroid dehydrogenase or "DH" for short may be classified as consisting of two types—Type I and Type II. The two types of enzyme, such as oestradiol 17β-hydroxysteroid dehydrogenases (E2HSD), have pivotal roles in regulating the availability of ligands to interact with the oestrogen receptor. Type I reduces oestrone (E1) to the biologically active oestrogen, oestradiol (E2) while E2HSD Type II inactivates E2 by catalysing its oxidation to E1.

DH Inhibition

It is believed that some disease conditions associated with DH activity are due to conversion of a nonactive, oestrone to an active, oestradiol. In disease conditions associated with DH activity, it would be desirable to inhibit DH activity.

Here, the term "inhibit" includes reduce and/or eliminate and/or mask and/or prevent the detrimental action of DH.

DH Inhibitor

In accordance with the present invention, the compound of the present invention is capable of acting as an DH inhibitor.

Here, the term "inhibitor" as used herein with respect to the compound of the present invention means a compound that can inhibit DH activity—such as reduce and/or eliminate and/or mask and/or prevent the detrimental action of DH. The DH inhibitor may act as an antagonist.

The ability of compounds to inhibit steroid dehydrogenase activity can be assessed using either T47D breast cancer cells in which E2HSD Type I activity is abundant or MDA-MB-231 cells for Type II inhibitor studies. In both cell lines formation of products is linear with respect to time and cell numbers. Details on a suitable Assay Protocol are presented in the Examples section.

It is to be noted that the compound of the present invention may have other beneficial properties in addition to or in the alternative to its ability to inhibit DH activity.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If $R^1$ is a sulphamate group then the compound of the present invention is referred to as a sulphamate compound.

Typically, the sulphamate group has the formula:

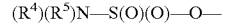

$(R^4)(R^5)N$—$S(O)(O)$—$O$— wherein preferably $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ may both be methyl. When $R^4$ and/or $R^5$ is aryl, typical values are phenyl and tolyl ($PhCH_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of $R^4$ and $R^5$ is H.

In some further preferred embodiments, each of $R^4$ and $R^5$ is H.

Phosphonate Group

If $R^1$ is a phosphonate group then the compound of the present invention is referred to as a phosphonate compound.

Typically, the phosphonate group has the formula:

$(R^6)$—P(O)(OH)—O— wherein preferably $R^6$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^6$ is alkyl, $R^6$ may be a lower alkyl groups containing from 1 to 6 carbon atoms, that is to say methyl, ethyl, propyl etc. By way of example, $R^6$ may be methyl. When $R^6$ is aryl, typical values are phenyl and tolyl (PhCH$_3$; o). Where $R^6$ represents cycloalkyl, typical values are cyclopropyl, cyclopentyl, cyclohexyl etc. $R^6$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If $R^1$ is a thiophosphonate group then the compound of the present invention is referred to as a thiophosphonate compound.

Typically, the thiophosphonate group has the formula:

$(R^7)$—P(S)(OH)—O— wherein preferably $R^7$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^7$ is alkyl, $R^7$ may be a lower alkyl groups containing from 1 to 6 carbon atoms, that is to say methyl, ethyl, propyl etc. By way of example, $R^7$ may be methyl. When $R^7$ is aryl, typical values are phenyl and tolyl (PhCH$_3$; o). Where $R^7$ represents cycloalkyl, typical values are cyclopropyl, cyclopentyl, cyclohexyl etc. $R^7$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If $R^1$ is a sulphonate group then the compound of the present invention is referred to as a sulphonate compound.

Typically, the sulphonate group has the formula:

$(R^8)$—S(O)(O)—O— wherein preferably $R^8$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^8$ is alkyl, $R^8$ may be a lower alkyl groups containing from 1 to 6 carbon atoms, that is to say methyl, ethyl, propyl etc. By way of example, $R^8$ may be methyl. When $R^8$ is aryl, typical values are phenyl and tolyl (PhCH$_3$; o). Where $R^8$ represents cycloalkyl, typical values are cyclopropyl, cyclopentyl, cyclohexyl etc. $R^8$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Combination of Sulphonate/Phosphonate/Thiophosphonate/Sulphamate

For some compounds of the present invention there may be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention may comprise one sulphamate group and one phosphonate group.

If these compounds of the present invention are based on a steroidal nucleus, preferably the other of said groups is located at position 17 of the steroidal nucleus.

Hydrocarbyl

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Assay for Determining STS Activity Using Cancer Cells

Protocol 1

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (MacIndoe et al. Endocrinology, 123, 1281-1287 (1988); Purohit & Reed, Int. J. Cancer, 50, 901-905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1\times10^5$ cells/flask using the above medium. Cells are grown to 80% confluency and the medium is changed every third day.

Intact monolayers of MCF-7 cells in triplicate 25 cm$^2$ tissue culture flasks are washed with Earle's Balanced Salt Solution (EBSS from ICN Flow, High Wycombe, U.K.) and incubated for 3-4 hours at 37° C. with 5 pmol ($7\times10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7\times10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 2

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then resuspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C]oestrone (7×103 dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3

Inhibition of Oestrone Sulphatase Activity in Vivo

The compounds of the present invention may be studied using an animal model, in particular in ovariectomised rats. In this model compounds which are oestrogenic stimulate uterine growth.

The compound (10 mg/Kg/day for five days) was administered orally to rats with another group of animals receiving vehicle only (propylene glycol). A further group received the compound EMATE subcutaneously in an amount of 10 µg/day for five days. At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

Lack of in Vivo Oestrogenicity

The compounds of the present invention may be studied using an animal model, in particular in ovariectomised rats. In this model, compounds which are oestrogenic stimulate uterine growth.

The compound (10 mg/Kg/day for five days) was administered orally to rats with another group of animals receiving vehicle only (propylene glycol). A further group received the estrogenic compound EMATE subcutaneously in an amount of 10 µg/day for five days. At the end of the study uteri were obtained and weighed with the results being expressed as uterine weight/whole body weight×100.

Compounds having no significant effect on uterine growth are not oestrogenic.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include, but are not limited to sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4hydroxyandrostenedione (4-OHA)) and/or steroids—such as the naturally occurring sterneurosteroids dehydroepiandrosterone sulphate (DHEAS) and pregnenolone sulphate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes, but not limited to cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, L-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Low Dosing Frequency

According to a very highly preferred aspect, the compounds of the invention may be administered in a dosage regimen which is less frequent than daily. Surprisingly, it has been found that the compounds of the invention display extraordinary duration of action compared with known steroid sulphatase inhibitors.

Accordingly, the invention provides a method of administering a compound of the invention comprising a continuous dosing schedule having a dosing interval selected from the group consisting of weekly dosing, twice weekly dosing, biweekly dosing, twice-monthly dosing and monthly.

Further, the invention provides a method of administering a compound of the invention comprising a continuous dosing schedule having a dosing periodicity ranging from about once every 3 days to about once every 16 days.

Preferably, the continuous dosing schedule is maintained until the desired therapeutic effect is achieved.

By once-weekly dosing is meant that a unit dosage of the compound of the invention is administered once a week, i.e. one time during a seven day period, preferably on the same day of each week. In the once weekly dosing regimen, the unit dosage is generally administered about every seven days. A non-limiting example of a once-weekly dosing regimen would entail the administration of a unit dosage of the compound of the invention every Sunday. It is preferred that the unit dosage is not administered on consecutive days, but the once-weekly dosing regimen can include a dosing regimen in which unit dosages are administered on two consecutive days falling within two different weekly periods.

Approximate effective dose rates may be in the range from 1 to 1000 mg/week, such as from 10 to 900 mg/week or even from 100 to 800 mg/week depending on the individual activities of the compounds in question and for a patient of average (70 Kg) bodyweight. More usual dosage rates for the preferred and more active compounds will be in the range 200 to 800 mg/week, more preferably, 200 to 500 mg/week, most preferably from 200 to 250 mg/week. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single weekly dosage rates in the range 200 to 800 mg, preferably 200 to 500, more preferably 200 to 250 mg.

By twice-weekly dosing is meant that a unit dosage of the of the compound of the invention is administered twice a week, i.e. two times during a seven day period, preferably on the same two days of each weekly period. In the twice-weekly dosing regimen, each unit dosage is generally administered about every three to four days. A non-limiting example of a twice-weekly dosing regimen would entail the administration of a unit dosage of the compound of the invention every Sunday and Wednesday. It is preferred that the unit dosages are not administered on the same or consecutive days, but the twice-weekly dosing regimen can include a dosing regimen in which unit dosages are administered on two consecutive days within a weekly period or different weekly periods.

Approximate effective dose rates may be in the range from 1 to 1000 mg/twice weekly, such as from 10 to 900 mg/twice weekly or even from 100 to 800 mg/twice weekly depending on the individual activities of the compounds in question and for a patient of average (70 Kg) bodyweight. More usual dosage rates for the preferred and more active compounds will be in the range 200 to 800 mg/twice weekly, more preferably, 200 to 500 mg/twice weekly, most preferably from 200 to 250 mg/twice weekly. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single twice weekly dosage rates in the range 200 to 800 mg, preferably 200 to 500, more preferably 200 to 250 mg.

By biweekly dosing is meant that a unit dosage of the of the compound of the invention is administered once during a two week period, i.e. one time during a fourteen day period, preferably on the same day during each two week period. In the twice-weekly dosing regimen, each unit dosage is generally administered about every fourteen days. A non-limiting example of a biweekly dosing regimen would entail the administration of a unit dosage of the compound of the invention every other Sunday. It is preferred that the unit dosage is not administered on consecutive days, but the biweekly dosing regimen can include a dosing regimen in which the unit dosage is administered on two consecutive days within two different biweekly periods.

Approximate effective dose rates may be in the range from 1 to 1000 mg/biweekly, such as from 10 to 900 mg/biweekly or even from 100 to 800 mg/biweekly depending on the individual activities of the compounds in question and for a patient of average (70 Kg) bodyweight. More usual dosage rates for the preferred and more active compounds will be in the range 200 to 800 mg/biweekly, more preferably, 200 to 500 mg/biweekly, most preferably from 200 to 250 mg/biweekly. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single biweekly dosage rates in the range 200 to 800 mg, preferably 200 to 500, more preferably 200 to 250 mg.

By twice-monthly dosing is meant that a unit dosage of the of the compound of the invention is administered twice, i.e. two times, during a monthly calendar period. With the twice-monthly regimen, the doses are preferably given on the same two dates of each month. In the twice-monthly dosing regimen, each unit dosage is generally administered about every fourteen to sixteen days. A non-limiting example of a twice-monthly dosing regimen would entail dosing on or about the first of the month and on or about the fifteenth, i.e. the midway point, of the month. It is preferred that the unit dosages are not administered on the same or consecutive days but the twice-monthly dosing regimen can include a dosing regimen in which the unit dosages are administered on two consecutive days within a monthly period, or different monthly periods. The twice-monthly regimen is defined herein as being distinct from, and not encompassing, the biweekly dosing regimen because the two regimens have a different periodicity and result in the administration of different numbers of dosages over long periods of time. For example, over a one year period, a total of about twenty four dosages would be administered according to the twice-monthly regimen (because there are twelve calendar months in a year), whereas a total of about twenty six dosages would be administered according to the biweekly dosing regimen (because there are about fifty-two weeks in a year).

Approximate effective dose rates may be in the range from 1 to 1000 mg/twice-month, such as from 10 to 900 mg/twice-month or even from 100 to 800 mg/twice-month depending on the individual activities of the compounds in question and for a patient of average (70 Kg) bodyweight. More usual dosage rates for the preferred and more active compounds will be in the range 200 to 800 mg/twice-month, more preferably, 200 to 500 mg/twice-month, most preferably from 200 to 250 mg/twice-month. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single twice-monthly dosage rates in the range 200 to 800 mg, preferably 200 to 500, more preferably 200 to 250 mg.

By monthly dosing is meant that a unit dosage of the compound of the invention is administered once, i.e. one time, during a monthly calendar period. With the monthly regimen, the doses are preferably given on the same date of each month. In the monthly dosing regimen, each unit dosage is generally administered about every twenty eight to thirty two days.

Approximate effective dose rates may be in the range from 1 to 1000 mg/month, such as from 10 to 900 mg/month or even from 100 to 800 mg/month depending on the individual activities of the compounds in question and for a patient of average (70 Kg) bodyweight. More usual dosage rates for the preferred and more active compounds will be in the range 200 to 800 mg/month, more preferably, 200 to 500 mg/month, most preferably from 200 to 250 mg/month. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single monthly dosage rates in the range 200 to 800 mg, preferably 200 to 500, more preferably 200 to 250 mg.

In a highly preferred embodiment, the invention provides a method for treating a condition or disease associated with steroid sulphatase in a mammal in need thereof said method comprising administering to said mammal a pharmaceutically effective amount of a compound of the invention as a unit dosage according to a schedule having a dosing interval of greater than daily. Preferably, the dosing interval is selected from the group consisting of once weekly dosing, twice-weekly dosing, biweekly dosing, twice-monthly dosing and monthly dosing. Very preferably, the dosing interval is once weekly dosing.

In an alternative highly preferred embodiment, the invention provides a method for treating a condition or disease associated with adverse STS levels in a mammal in need thereof said method comprising administering to said mammal a pharmaceutically effective amount of a compound of the invention as a unit dosage according to a schedule having a dosing interval of greater than daily. Preferably, the dosing interval is selected from the group consisting of once weekly dosing, twice-weekly dosing, biweekly dosing, twice-monthly dosing and monthly dosing. Very preferably, the dosing interval is once weekly dosing.

In an alternative highly preferred embodiment, the invention provides a method for treating cancer in a mammal in need thereof said method comprising administering to said mammal a pharmaceutically effective amount of a compound of the invention as a unit dosage according to a schedule having a dosing interval of greater than daily. Preferably, the dosing interval is selected from the group consisting of once weekly dosing, twice-weekly dosing, biweekly dosing, twice-monthly dosing and monthly dosing. Very preferably, the dosing interval is once weekly dosing. Preferably, the cancer is selected from an endocrine dependent cancer. More preferably, the cancer is selected from cancer of the breast, endometrium or prostate, most preferably the breast.

In an alternative highly preferred embodiment, the invention provides a method for treating cancer in a mammal in need thereof said method comprising administering to said mammal a pharmaceutically effective amount of a compound of the invention as a unit dosage according to a schedule having a dosing interval of greater than daily. Preferably, the dosing interval is selected from the group consisting of once weekly dosing, twice-weekly dosing, biweekly dosing, twice-monthly dosing and monthly dosing. Very preferably, the dosing interval is once weekly dosing. Preferably, the cancer is selected from an endocrine dependent cancer. More preferably, the cancer is selected from cancer of the breast, endometrium or prostate, most preferably the breast.

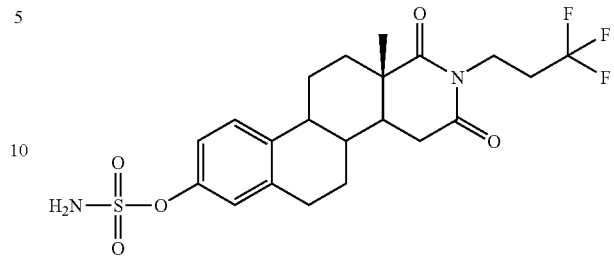

In an alternative highly preferred embodiment, the invention provides a method for treating breast cancer in a mammal in need thereof said method comprising administering to said mammal a pharmaceutically effective amount of a compound of formula

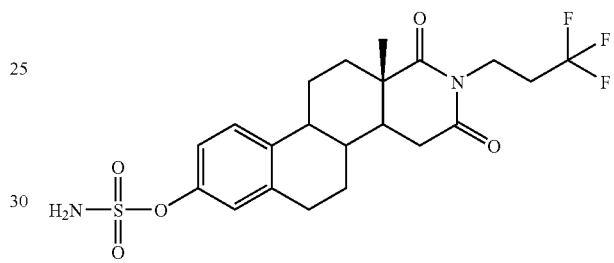

as a unit dosage according to a schedule having a dosing interval of once weekly dosing.

Treatment Kits

In further embodiments, the present invention relates to a kit for conveniently and effectively carrying out the methods in accordance with the present invention. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered. Alternatively, placebo dosages, or calcium or dietary supplements, either in a form similar to or distinct from the bisphosphonate dosages, can be included to provide a kit in which a dosage is taken every day.

Pharmaceutically Acceptable Salts

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulphuric, methanesulphonic, naphthalenesulphonic, benzenesulphonic, toluenesulphonic, camphorsulphonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, ostein<'>s deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

In a preferred embodiment, the compounds of the present invention are useful in the treatment of endocrine dependent cancers. Preferred endocrine dependent cancers are breast cancer, endometrial cancer, prostate cancer and ovarian cancer.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 5

Procedure
Stage 1
MCF-7 breast cancer cells are seeded into multi-well culture plates at a density of 105 cells/well. Cells were allowed to attach and grown until about 30% confluent when they are treated as follows:
Control—no treatment
Compound of Interest (COI) 20 μM
Cells are grown for 6 days in growth medium containing the COI with changes of medium/COI every 3 days. At the end of this period cell numbers were counted using a Coulter cell counter.
Stage 2
After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Assay for Determining DH Activity Using Cancer Cells

Protocol 6

Conversion of oestrone to oestradiol (E1→E2, E2DH Type I) and oestradiol to oestrone (E2→E1, E2DH Type II) was measured in intact cell monolayers of T47D and MDA-MB-231 breast cancer cells respectively. Cells were cultured in flasks until they were 80-90% confluent. $^3$H-E1 or $^3$H-E2 (6 pmol, ~90 Ci/mmol) were added to each flask in the absence (control) or presence of various test compounds (10 μM) in 2.5 ml of medium. Substrate was also added to flasks without cells and incubated in parallel (blanks).

After incubation with T47D cells for 30 min or MDA cells for 3 h at 37° C., 2 ml of the medium was added to test tubes containing $^{14}$C-E2 or $^{14}$C-E1 (~5000 cpm) and 50 μg E2 or E1 respectively. Steroids were extracted from the aqueous medium with diethyl ether (4 ml). The ether phase was decanted into separate tubes after freezing the aqueous phase in solid carbon dioxide-methanol mixture. The ether was evaporated to dryness under a stream of air at 40° C. The residue was dissolved in a small volume of diethyl ether and applied to TLC plates containing a fluorescent indicator. E1 and E2 were separated by TLC using DCM-Ethyl acetate (4:1 v/v). The position of the product from each incubation flask was marked on the TLC plate after visualisation under UV light. The marked regions were cut out and placed in scintillation vials containing methanol (0.5 ml) to elute the product. The amount of $^3$H-product formed and $^{14}$C-E1 or $^{14}$C-E2 recovered were calculated after scintillation spectrometry. The amount of product formed was corrected for procedural losses and for the number of cells in each flask.
Cancer
As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of oestrogen metabolites has been stimulated by the growing body of evidence that 2-methoxyoestradiol is an endogenous metabolite with anti-mitotic properties. 2-MeOE2 is formed from 2-hydroxy oestradiol (2-OHE2) by catechol oestrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 oestrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent antimitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being 100-times higher than that of oestradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurogenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz: disorders including but not limited to, androgen-dependent disorders of the pilosebaceous unit such as acne, seborrhea, androgenic alopecia and hirsutism; cancer, especially estrogen- and androgen-dependent tumors such as tumors of the breast, endometrium and prostate, and squamous cell carcinoma; inflammatory and autoimmune diseases such as rheumatoid arthritis, type I and II diabetes, systemic lupus erythematosus, multiple sclerosis, myastenia gravis, thyroiditis, vasculitis, ulcerative colitis and Crohn's disease; skin disorders such as psoriasis, eczema and contact dermatitis; graft versus host disease; asthma; organ rejection following transplantation; and for enhancement of cognitive function, as in senile dementia, including Alzheimer's disease.

In addition, or in the alternative, the compound or composition of the present invention may be useful in the treatment of the disorders listed in WO-A-98/05635. For ease of reference, part of that list is now provided, however the present invention may be useful in the treatment of each disorder listed in WO-A-98/05635, including those not recited here: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including but not limited to infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including but not limited to arthritis, rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreoretinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Sulphamate Compound Preparation

The sulphamate compounds of the present invention may be prepared by reacting an appropriate alcohol with a suitable chloride. By way of example, the sulphamate compounds of the present invention may be prepared by reacting an appropriate alcohol with a suitable sulphamoyl chloride, of the formula $R^4R^5NSO_2Cl$.

Typical conditions for carrying out the reaction are as follows.

Sodium hydride and a sulphamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulphamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

Summary

In summation, the present invention provides compounds for use as steroid sulphatase inhibitors and/or steroid dehydrogenase inhibitors, and pharmaceutical compositions for the same.

EXAMPLES

The present invention will now be further described by way of the following non-limiting examples.

Example

Summary

Breast cancer is a disease of major importance in Europe and Northern America. In Britain, it kills more people than any other type of cancer. Hormone dependant breast cancer represents about two third of those cases in postmenopausal women; it corresponds to a type of breast cancer in which tumours rely on estrogens for their growth and development.

Endocrine therapy, where oestrogen circulating levels are controlled via the use of drugs that inhibit one or several enzymatic pathway in oestrogen biosynthesis, is the response for HDBC. Different targets can be considered and most of the work has been done around antiestrogens and aromatase inhibitors. The enzymes steroid sulphatase and 17β-HSD type 1 have later emerged as potent targets.

While several potent inhibitors have been developed for STS, 17β-HSD type 1 has not raised as much interest and only few active molecules have been reported. Relying on the fact that D-ring derivatives of EMATE are potent inhibitors of 17β-HSD type 1, we initiated the design and synthesis of analogs of EMATE with reduced estrogenicity. This has led to a series of compounds where the D-ring is a piperidine dione moiety and where the N-atom is bearing a variety of side-chains.

Biological testing against STS, which was performed on breast cancer cells, revealed a very high activity for derivatives bearing a propyl or a picolyl side-chain. With an $IC_{50}$ of 1 nM, they are much more potent than EMATE.

Experimental

1—General Methods

All chemicals were either purchased from Aldrich Chemical Co. (Gillingham, Dorset, UK) or Lancaster Synthesis (Morecambe, Lancashire, U.K.). All organic solvents of A. R. grade were supplied by Fisons plc (Loughborough, U.K.). Anhydrous N,N-dimethylformamide (DMF) and N,N-dimethylacetamide (DMA), respectively used for all N-alkylations and sulphamoylation reactions, were purchased from Aldrich and were stored under a positive pressure of $N_2$ after use. Sulphamoyl chloride was prepared by an adaptation of the method of Apel and Berger[48] and was stored as a solution in toluene as described by Woo et al.[16] An appropriate volume of this solution was freshly concentrated in vacuo immediately before use.

E1S and E1 were purchased from Sigma Chemical Co. (Poole, U.K.). [6,7-$^3$H]E1S (specific activity, 50 Ci/mmol) and [4-$^{14}$C]E1 (specific activity, 52 mCi/mmol) were purchased from New England Nuclear (Boston, Mass.). [6,7-$^3$H] E1 (specific activity, 97 Ci/mmol) was obtained from the Amersham International Radiochemical Centre (Amersham, U.K.).

Thin layer chromatography (TLC) was performed on pre-coated plates (Merck TLC aluminium sheets silica gel 60 $F_{254}$, Art. No. 5554). Product(s) and starting material (SM) were detected by either viewing under UV light or treating with a methanolic solution of phosphomolybdic acid followed by heating. Flash column chromatography was performed on silica gel (Sorbsil C60). IR spectra were determined as KBr discs using a Perkin-Elmer Spectrum RXI FT-IR and peak positions are expressed in cm$^{-1}$. $^1$H NMR and DEPT-edited $^{13}$C NMR spectra were recorded with JMN-GX 400 NMR spectrometers, and chemical shifts are reported in parts per million (ppm, δ) relative to tetramethylsilane (TMS) as an internal standard. The following abbreviations are used to describe resonances in $^1$H NMR and $^{13}$C NMR spectra: br, broad; s, singlet; d, doublet; t, triplet; q, quartet; m, multiplet and combinations such as dd, doublet of doublets. Chemical shifts for AB systems ($δ_A$ and $δ_B$) were approximated by taking the middle of each doublet and the corresponding coupling constant labelled $J_{AB}$ or $J_{BA}$. As an example, $δ_A$ and $δ_B$ were calculated following the formula shown in appendix 2 for compound 21. HPLC analysis was performed on a Waters Millenium$^{32}$ instrument equipped with a Waters 996 PDA detector. The traces were recorded on a Waters Radial-pack C18, 8×100 mm column eluted with a methanol/water gradient at 2 mL/min. Mass spectra were recorded at the Mass Spectrometry Service Center, University of Bath. FAB-MS were carried out using m-nitrobenzyl alcohol (NBA) as the matrix, and elemental analyses were performed by the Microanalysis Service, University of Bath. Melting points were determined using a Reichert-Jung Thermo Galen Kofler block and are uncorrected.

3-Benzyloxy-estrone

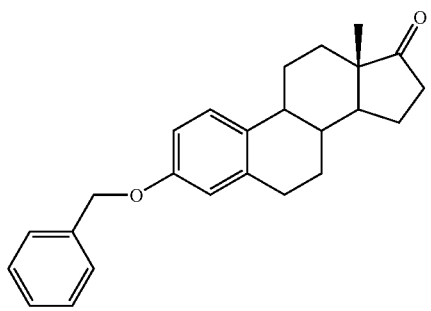

Sodium hydride (60% dispersion in mineral oil, 0.68 g, 20.34 mmol) was added to a stirred solution of estrone (5.0 g, 18.49 mmol) in anhydrous DMF (50 mL) at 0° C. under an atmosphere of $N_2$ and the resulting suspension was stirred for 1 hour. Benzyl bromide (2.42 mL, 20.34 mmol) was then added and the reaction mixture was heated at 80° C. for 4 hours. The resulting solution was poured into ice/water and the organic fraction that separated was extracted into ethyl acetate (150 mL), washed with water (4×50 mL), dried (MgSO$_4$), filtered and evaporated in vacuo. The resulting pale yellow crude was recrystallized from isopropyl alcohol to give 3-benzyloxy-estrone as white flaky crystals (4.73 g, 71%): mp 129-131° C. [lit.[26] (petroleum ether) 132-134° C.]. IR (KBr) $v_{max}$ 3100, 2950-2840, 1730, 1600, 1500 cm$^{-1}$. $^1$H NMR (CDCl$_3$) δ 0.91 (3H, s, C-18-H$_3$), 1.41-2.54 (13H, m), 2.86-2.93 (2H, m, C-6-H$_2$), 5.04 (2H, s, OCH$_2$Ar), 6.73 (1H, d, J=2.5 Hz, C-4-H), 6.80 (1H, dd, J=8.6 Hz and J=2.5 Hz, C-2-H), 7.20 (1H, d, J=8.6 Hz, C-1-H) and 7.30-7.44 (5H, m, C$_6$H$_5$).

3-Benzyloxy-marrianolic acid

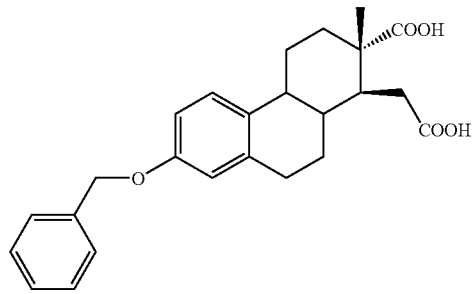

A solution of iodine (7.6 g, 29.94 mmol) in 95 mL of MeOH and a solution of KOH (13.7 g) in 27 mL of water and 61 mL of MeOH were added dropwise and alternatively to a stirred solution of 2-benzyloxy-estrone (3.8 g, 10.54 mmol) in MeOH (1 L) so that the colour of the mix remains orange/brown. The addition was carried out over 45 minutes and the resulting light yellow solution was stirred overnight at room temperature under an atmosphere of $N_2$. The mixture was then concentrated and poured into water (800 mL). After acidification with HCl 5M, the organic fraction was extracted into ether (600 mL), washed with aqueous sodium thiosulfate (4×100 mL), water (4×100 mL), dried (MgSO$_4$), filtered and evaporated in vacuo. The resulting yellow foam (4.54 g) was then dissolved in a solution of KOH (7.6 g) in MeOH/H$_2$O 1:2 (228 mL) and heated to reflux for 4 hours. The final brown mixture was poured into water (800 mL) and after acidification with 5M HCl the organics were extracted into ethyl acetate (300 mL). After washing with brine (4×200 mL), the organic layer was dried (MgSO$_4$), filtered and evaporated in vacuo to give a yellow residue (4.32 g). This was recrystallized from chloroform/hexane 5:3 to give 3-benzyloxy-marrianolic acid as a creamy powder (3.25 g, 75%): mp 212-215° C. [lit.[18] (aq. MeOH) 226-227° C.]. IR (KBr) $v_{max}$ 3050-2650, 1700, 1600-1500 cm$^{-1}$. $^1$H NMR (DMSO-d$_6$) δ 1.02 (3H, s, C-18-H$_3$), 1.20-2.78 (11H, m), 2.72-2.76 (2H, m, C-6-H$_2$), 5.05 (2H, s, OCH$_2$Ar), 6.68 (1H, d, J=2.5 Hz, C-4-H), 6.75 (1H, dd, J=8.7 Hz and J=2.5 Hz, C-2-H), 7.18 (1H, d, J=8.7 Hz, C-1-H), 7.30-7.42 (5H, m, C$_6$H$_5$) and 12.14 (2H, s, CO$_2$H); $^{13}$C NMR (DMSO-d$_6$) δ 15.4 (q), 25.8, 26.5, 29.7, 35.8, 36.1 (all t), 40.7, 41.8, 42.5 (all d), 46.2 (s), 68.9 (t), 112.3, 114.0, 126.3, 127.3 (2×), 127.5, 128.2 (2×) (all d), 131.6, 137.2 (2×), 156.0, 173.9 and 178.6 (all s). MS m/z (FAB+) 408.2 [41, M$^+$], 91.1 [100, (CH$_2$Ar)$^+$]. HRMS m/z (FAB+) calcd for C$_{25}$H$_{28}$O$_5$: 408.1937. Found: 408.1940.

3-Benzyloxy-16,17-seco-estra-1,3,5(10)-triene-16,17-imide

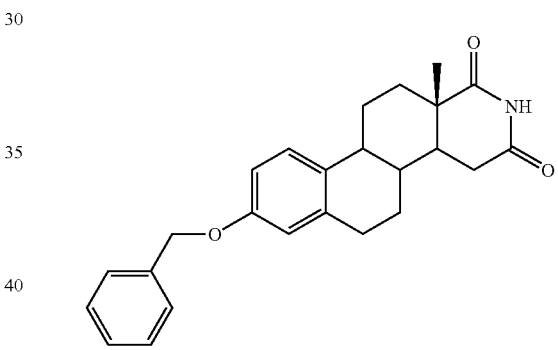

3-Benzyl-marrianolic acid (3.25 g, 7.96 mmol) and urea (3.25 g, 54.11 mmol) were heated at 180° C. under an atmosphere of $N_2$ for 45 minutes. The resulting brown residue was crushed and acetone added (200 mL) to give a brown suspension. This mixture was concentrated to ca 100 mL, silica gel was added and the solvent removed. The resulting powder was transferred onto a flash chromatography column. Elution with chloroform/acetone (96:4) gave 3-benzyloxy-16,17-seco-estra-1,3,5(10)-triene-16,17-imide as a white solid (2.75 g, 89%). For analysis, a sample was recrystallized from EtOH to give colourless needles: mp 225-226° C. IR (KBr) $v_{max}$ 3260, 2900-2870, 1720, 1700, 1600-1500 cm$^{-1}$. $^1$H NMR (DMSO-d$_6$) δ 1.09 (3H, s, C-18-H$_3$), 1.20-2.72 (11H, m), 2.76-2.80 (2H, m, C-6-H$_2$), 5.05 (2H, s, OCH$_2$Ar), 6.72 (1H, d, J=2.5 Hz, C-4-H), 6.76 (1H, dd, J=8.7 Hz and J=2.5 Hz, C-2-H), 7.19 (1H, d, J=8.7 Hz, C-1-H), 7.31-7.44 (5H, m, C$_6$H$_5$) and 10.63 (1H, s, NH); $^{13}$C NMR (DMSO-d$_6$) δ 16.2 (q), 25.1, 25.2, 29.2, 32.4, 32.7 (all t), 37.8, 40.3 (all d), 40.5 (s), 41.9 (d), 68.9 (t), 112.2, 114.1, 126.0, 127.3 (2×), 127.4, 128.2 (2×) (all d), 131.5, 137.0, 137.1, 156.0, 172.1 and 178.9 (all s). MS m/z (FAB+) 390.2 [58, (M+H)$^+$], 91.1 [100, (CH$_2$Ar)$^+$]. HRMS m/z (FAB+) calcd for C$_{25}$H$_{28}$NO$_3$: 390.2069. Found: 390.2059. Anal. calcd for C$_{25}$H$_{27}$NO$_3$: C, 77.09; H, 6.99; N, 3.60. Found: C, 76.90; H, 6.99; N, 3.73.

3-Benzyloxy-N-(3,3,3-trifluoropropyl)-16,17-seco-estra-1,3,5(10)-triene-16,17-imide (CMS01179)

$C_{28}H_{30}F_3NO_3$ MW 485.54

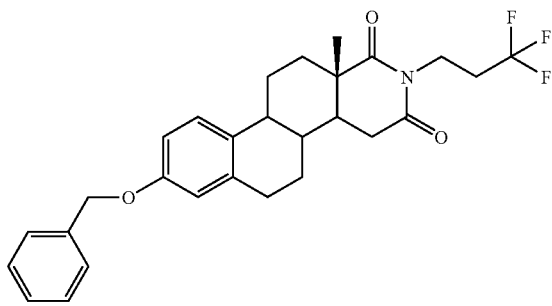

To a solution of 3-benzyloxy-16,17-seco-estra-1,3,5(10)-triene-16,17-imide (2.0 g, 5.14 mmol), in anhydrous acetonitrile (250 mL) was added potassium carbonate (0.780 g, 5.66 mmol, 1.1 eq), potassium iodide (0.1 g) 3-bromo-1,1,1-trifluoropropane (1.61 g, 10.3 mmol, 2 eq and 18-crown-6 (2.98 g, 11.31 mmol, 2.2 eq), and the reaction heated at 82° C. for 24 hours. After cooling and evaporation on the acetonitrile, the resulting orange foam was redissolved in ethyl acetate (200 mL) and washed with brine (2×200 mL) dried over magnesium sulphate and evaporated. Flash chromatography (200 g silica using 5 cm Ø column, flushed with 20% ethyl acetate/hexanes) eluted the title compound as a white crystalline solid (1.36 g, 54%);

mp 180-182° C.;
$R_f$: 0.52 (20% ethyl acetate/hexanes);
$^1$H NMR (270 MHz, CDCl$_3$) δ 1.38 (3H, s, 18-CH$_3$), 1.10-2.00 (6H, m), 2.20-2.50 (6H, m), 2.80-2.90 (2H, m), 2.97 (1H, dd, J=4.7 and 8.3 Hz) 3.90-4.20 (2H, m, CH$_2$—CF$_3$), 5.02 (2H, s, O—CH$_2$) 6.71 (1H, d, J=2.7 Hz, 4-CH), 6.79 (1H, dd, J=2.7 and 8.5 Hz, 2-CH) and 7.20 (1H, d, J=8.5 Hz, 1-CH) and 7.30-7.50 (5H, m, 5×ArH);
$^{13}$C NMR (67.9 MHz, CDCl$_3$) δ 16.8 (CH$_3$), 25.5, 25.8 and 29.7 (all CH$_2$), 31.9 (q, J=29.3 Hz, CH$_2$CF$_3$), 33.3, 33.5 and 33.7 (all CH$_2$), 38.6 and 40.3 (both CH), 41.6 (CH$_2$), 42.5 (CH), 70.0 (O—CH$_2$), 112.8, 114.7 and 126.4 (all CH), 127.5 (2×CH), 128.0 (CH) and 128.7 (2×CH), 131.6, 137.1, 137.5, 157.1, 171.6 and 178.2 (all C);
$^{19}$F NMR (376 MHz, CDCl$_3$) δ −65.30 (3F, t, J=10.53 Hz CF$_3$);
HPLC (70% CH$_3$CN in H$_2$O) t$_r$=XXX (100%);
LCMS (AP$^-$), m/z 394.26 (M$^-$, 100%).
Anal. Calcd. for $C_{28}H_{30}F_3NO_3$: C, 69.26; H, 6.23; N, 2.28. Found: C, H, N %.

3-Hydroxy-N-(3,3,3-trifluoropropyl)-16,17-seco-estra-1,3,5(10)-triene-16,17-imide (CMS01181, STX1937)

$C_{21}H_{24}F_3NO_3$ MW 395.42

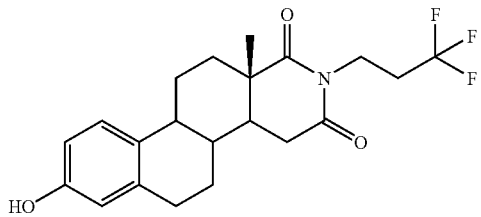

A solution of 3-Benzyloxy-N-(3,3,3-trifluoropropyl)-16,17-seco-Estra-1,3,5(10)-triene-16,17-imide (1.10 g, 2.27 mmol) with 10% Pd/C (0.10 g) in methanol (40 mL) and tetrahydrofuran (40 mL) was stirred under an atmosphere of hydrogen for 3 hours. After removal of the catalyst by filtration through a celite pad, evaporation of the solvent gave a white solid. Recrystallisation (diethyl ether/hexane) gave the title compound as white crystalline solid (0.870 g, 97%);

mp 194-196° C.;
$R_f$: 0.41 (20% ethyl acetate/hexanes);
$^1$H NMR (270 MHz, CDCl$_3$) δ 1.16 (3H, s, 18-CH$_3$), 1.20-1.60 (3H, m), 1.65-2.00 (3H, m), 2.20-2.50 (6H, m), 2.80-2.90 (2H, m), 2.96 (1H, dd, J=4.7 and 8.3 Hz) 3.90-4.20 (2H, m, CH$_2$—CF$_3$), 6.57 (1H, d, J=2.5 Hz, 4-CH), 6.64 (1H, dd, J=2.5 and 8.4 Hz, 2-CH) and 7.15 (1H, d, J=8.4 Hz, 1-CH);
$^{13}$C NMR (67.9 MHz, CDCl$_3$) δ16.3 (CH$_3$), 25.5, 25.7 and 29.5 (all CH$_2$), 31.9 (q, J=28.7 Hz, CH$_2$CF$_3$), 33.2 (q, J=3.1 Hz, CH$_2$CH$_2$CF$_3$), 33.5 and 33.7 (both CH$_2$), 38.6 and 40.2 (both CH), 41.6 (C), 42.4 (CH), 113.1 and 115.0 (both CH), Expected 126.0 (q, J=276.8 Hz, CF$_3$) but absent, 126.5 (CH), 131.4, 137.4, 153.6, 171.6 and 178.4 (all C);
$^{19}$F NMR (376 MHz, CDCl$_3$) δ −65.341 (3F, t, J=10.52 Hz, CF$_3$);
HPLC (70% CH$_3$CN in H$_2$O) t$_r$=2.58 min (95.15%);
LCMS (AP$^-$), m/z 394.26 (M$^-$, 100%).
Anal. Calcd. for $C_{21}H_{24}F_3NO_3$: C, 63.79; H, 6.12; N, 3.52. Found: C, H, N %
HRMS (ES+) Found 396.1765; $C_{21}H_{25}F_3NO_3$ (M+H)$^+$ requires 396.1781.

3-Sulfomoyloxy-N-(3,3,3-trifluoropropyl)-16,17-seco-Estra-1,3,5(10)-triene-16,17-imide (CMS01188, STX1938)

$C_{21}H_{25}F_3N_2O_5S$ MW 474.49

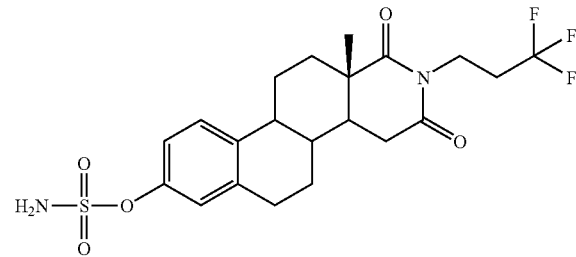

0.6M Sulphamoyl chloride in toluene (5.80 mL, 3.50 mmol, 2.5 eq.) was evaporated under reduced pressure at room temperature. The resulting white solid was dissolved in anhydrous N,N-dimethylacetamide (2.5 mL) and cooled to 0° C. under nitrogen. To this stirred solution was added in a dropwise manner a solution of 3-Hydroxy-N-(3,3,3-trifluoropropyl)-16,17-seco-Estra-1,3,5(10)-triene-16,17-imide (0.55 g, 1.39 mmol) in N,N-dimethylacetamide (2.5 mL) then the external cooling was removed and the reaction allowed to warm to room temperature overnight. The light brown suspension obtained was diluted with ethyl acetate (50 mL) and washed with saturated aqueous ammonium chloride solution (3×50 mL) and brine (50 mL) then dried over anhydrous magnesium sulphate, filtered and evaporated under reduced pressure. The resulting gum was dissolved in the minimum amount of dichloromethane (5 mL), diethyl ether (25 mL) was added then hexane (100 mL) was added in small amounts to initiate precipitation. The Recrystallisation (dichloromethane/hexanes) gave the title compound as white crystalline solid (0.584 g, 88%);

mp 192-194° C.;
$R_f$: 0.18 (20% ethyl acetate/hexanes);
$^1$H NMR (270 MHz, CDCl$_3$) δ 1.16 (3H, s, 18-CH$_3$), 1.20-2.00 (6H, m), 2.20-2.50 (6H, m), 2.85-2.95 (2H, m), 2.96 (1H, dd, J=4.7 and 8.3 Hz) 3.92-4.15 (2H, m, CH$_2$—CF$_3$), 4.97 (2H, s, NH$_2$), 7.05 (1H, d, J=2.5 Hz, 4-CH), 6.64 (1H, dd, J=2.5 and 8.5 Hz, 2-CH) and 7.15 (1H, d, J=8.5 Hz, 1-CH);

$^{13}$C NMR (67.9 MHz, CDCl$_3$) δ 16.3 (CH$_3$), 25.3, 25.4 and 29.3 (all CH$_2$), 31.9 (q, J=29.1 Hz, CH$_2$CF$_3$), 33.2 (q, J=3.8 Hz, CH$_2$CH$_2$CF$_3$), 33.4 and 33.5 (both CH$_2$), 38.0 and 40.2 (both CH), 41.4 (C), 42.6 (CH), 119.3 and 121.8 (both CH), 126.0 (q, J=276.8 Hz, CF$_3$), 126.8 (CH), 138.2, 138.25, 148.1, 171.3 and 178.1 (all C);

$^{19}$F NMR (376 MHz, CDCl$_3$) δ −65.317 (3F, t, J=10.52 Hz, CF$_3$);

HPLC (90% CH$_3$CN in H$_2$O) t$_r$=1.070 s (1.45%) t$_r$=1.921 s (98.55%);

LCMS (ES−) m/z 473.16 [(M−H)$^-$, 100%]

HRMS (ES+) Found 497.1325; C$_{21}$H$_{25}$F$_3$N$_2$NaO$_5$S (M+Na)$^+$ requires 497.1334HRMS (FAB+) calcd. for XXX (M)$^+$, found;

Anal. Calcd. for C$_{21}$H$_{25}$F$_3$N$_2$O$_5$S: C, 53.16; H, 5.13; N, 5.90. Found: C, H, N %.

Comparison of IC$_{50}$ Values of Compound of the Invention with Known Steroid Sulphatase Inhibitor.

The IC$_{50}$ values of STX1938 where measured in JEG-3 cells. The IC$_{50}$ for STX 1938 is 35 pM which compares with a value of 180 pM for STX213 measured in the same assay.

The structures of STX1938 and STX213 are shown for comparison:

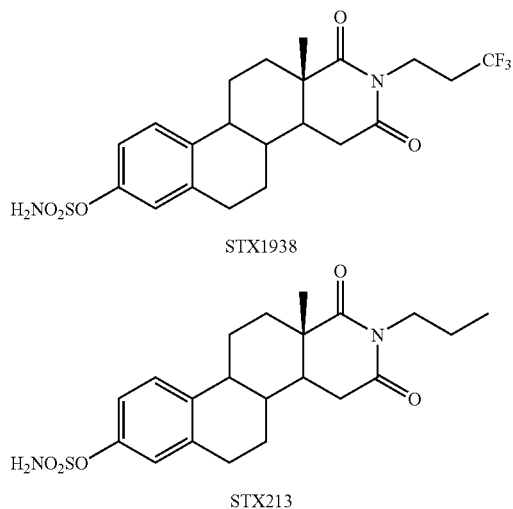

Figure 2:
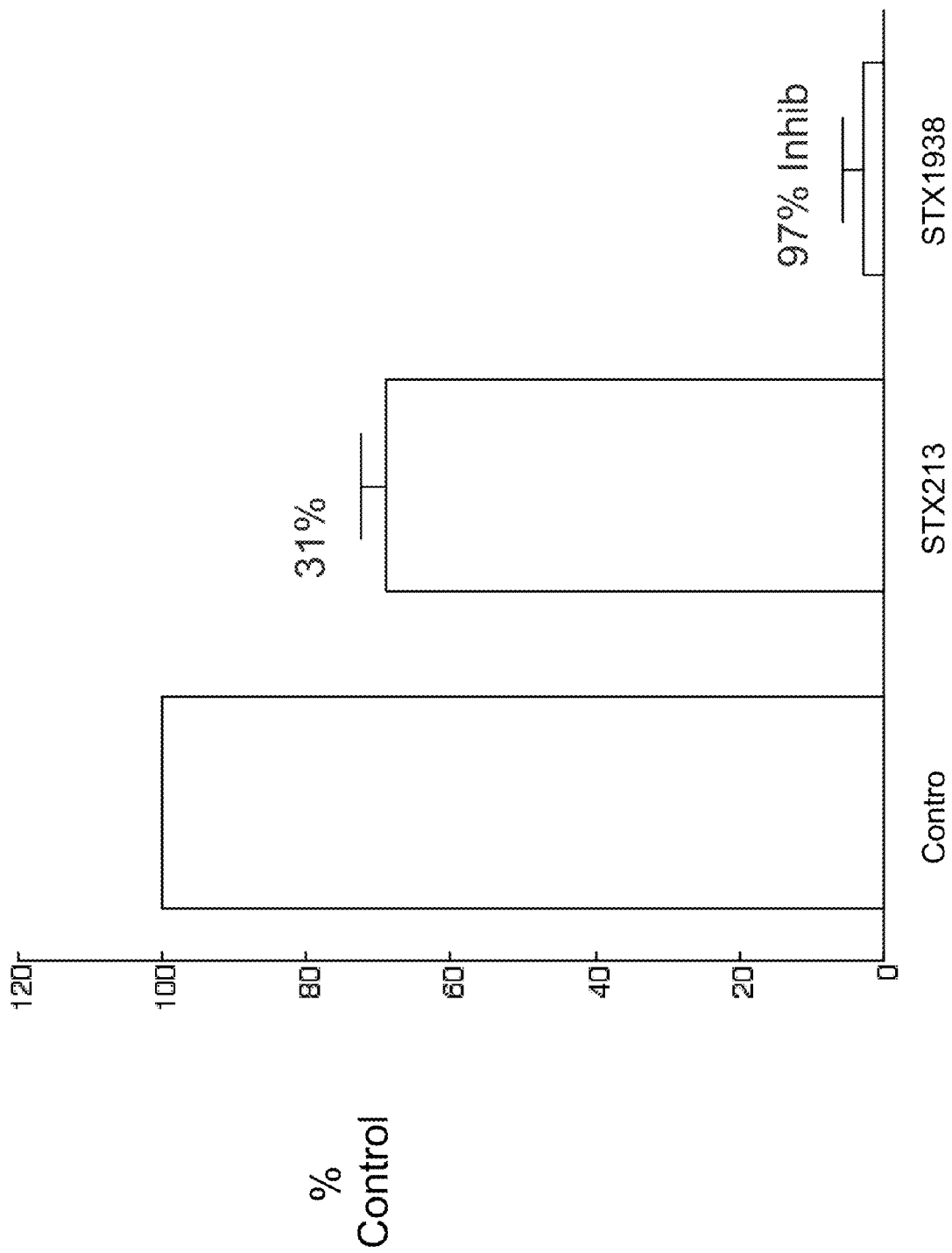
FIG. 2 shows the inhibition of STS activity in rat livers 15 days after a single p.o. dose of STX1938.

FIG. 2 shows the inhibition of STS activity in rat livers 15 days after a single p.o. dose of STX1938. For comparison, for STX213 STS activity had recovered by 69% i.e. still only 31% inhibition.

In Vivo Efficacy of STX1938
Test Procedure
MCF-7$_{STS}$ Cells (Cells Over Expressing STS)

MCF-7 cells were routinely cultured in RPMI with 10% FCS. The cDNAs for the STS was cloned into the pCI-Neo vector which contains the neomycin resistant gene and transfected into MCF-7 cells. Stable clones were selected using G418 and cell lines established and evaluated for enzyme expression and activity.

Mice

Ovariectomised, athymic female MF-1 nude mice (nu/nu) (age 6-8 weeks) were obtained from Harlan Olac. Twenty four hours before the inoculation of MCF-7$_{STS}$ cells animals were injected s.c. with estradiol sulphate (E2S). On the day of inoculation 5×10$^6$ MCF-7$_{STS}$ cells (50 μl in Matrigel) were injected s.c. into the right flank of the mice. After cell inoculation mice were injected with E2S (100 μg/50 μl) and received another injection of these steroids 24 h later. Mice then received E2S 3 times per week until the end of the study. When tumours had reached approximately 80 mm$^3$ dosing was initiated with compounds being administered orally (100 μl; vehicle 10% THF: 90% propylene glycol) at 1 mg/kg. Tumour measurements and the weight of animals were recorded weekly. Samples of tumour and liver tissues together with blood were collected at a number of time points after the cessation of dosing.

Study 1

Mice were dosed 5/7 days per week with STX1938 at 0.1 mg/kg, 1 mg/kg and 10 mg/kg p.o. for the duration of the study.

Study 2

To compare the efficacy of STX1938 versus STX64 mice were dosed once per week for 7 weeks with either compound at 1 mg/kg, p.o.

Tumours

Tumours were measured weekly and their volumes calculated using the equation length×width$^2$/2.

STS Activity Measurements

Samples of tumour or liver tissues were homogenised in phosphate buffered saline (pH 7.4 containing 250 mM sucrose). Duplicate aliquots were incubated for 4 h with [$^3$H-E1S] (53 Ci/mmol, 2-3 nM, Perkin Elmer, Boston Mass.) adjusted to a final concentration of 20 μM with unlabelled substrate (Sigma. Poole, Dorset, UK). [4-$^{14}$C] Oestrone was included in the reaction mixture to monitor procedural losses. At the end of the incubation period product oestrone was isolated from the reaction mixture by toluene partition. An aliquot of the toluene was removed and the $^3$H and $^{14}$C radioactivity measured by liquid scintillation spectrometry. The mass of oestrone sulphate hydrolysed was calculated form the $^3$H counts detected, corrected for procedural losses.

Plasma Oestradiol Concentrations

Plasma oestradiol concentrations were measured by a specific radioimmunoassay procedure.

Data Analysis

Student's t test was used to assess the significance of the differences in tumour volumes for the different groups.

Results
Study 1

Figure 3:
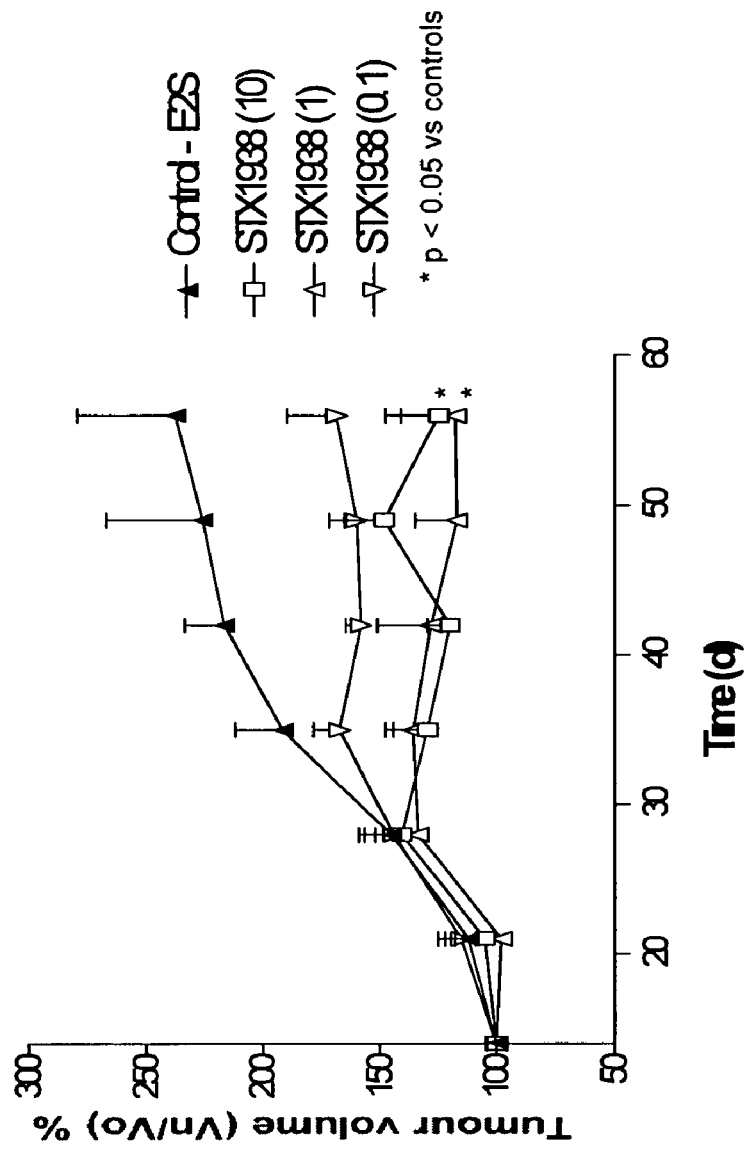
FIG. 3 shows the inhibition of tumour growth by STX1938 dosing 5/7 days per week.
Figure 4:
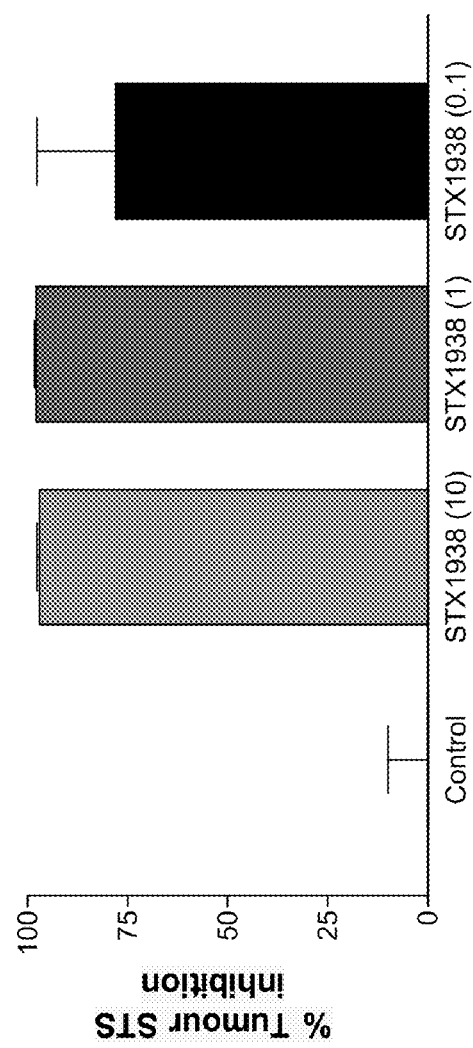
FIG. 4 shows the inhibition of tumour STS activity by STX1938 dosing 5/7 days per week.

Dosing with STX1938 at 1 mg/kg and 10 mg/kg significantly reduced the growth of E2S stimulated tumours in nude mice (FIG. 3). Tumour STS activity at the 1 mg/kg and 10 mg/kg doses was almost completely inhibited (FIG. 4).

Study 2

Figure 5:
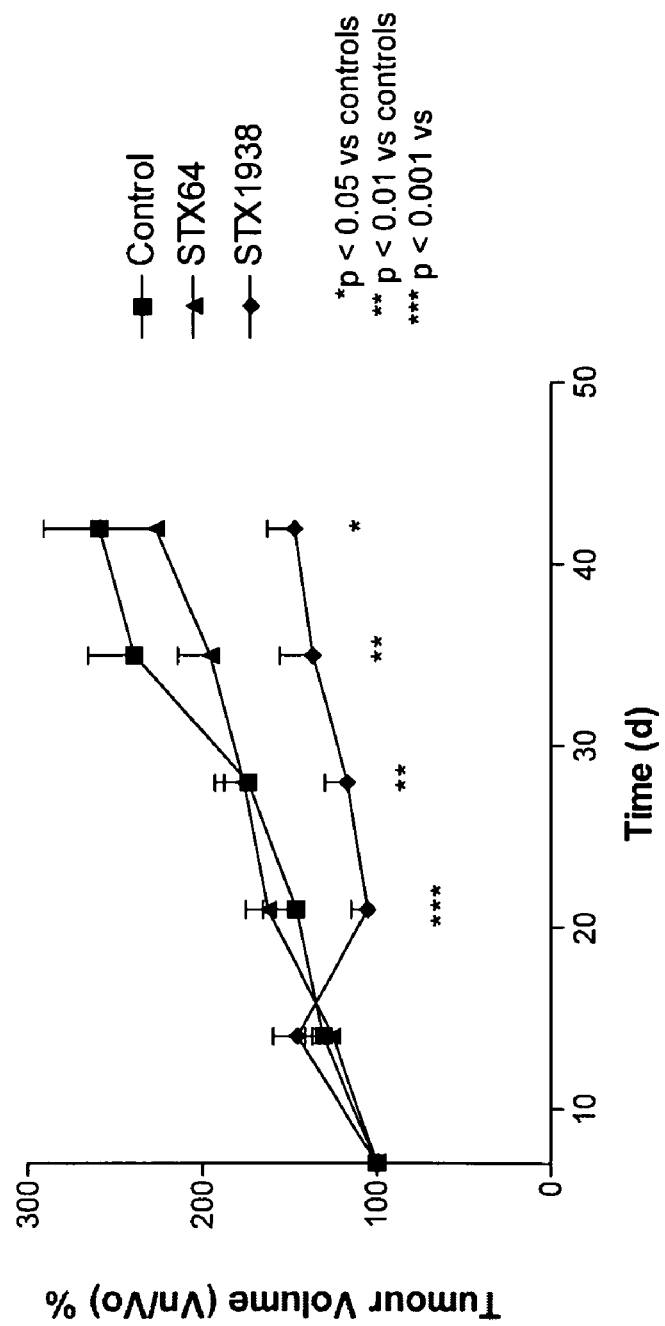
FIG. 5 shows the inhibition of tumour growth by STX1938 dosing once per week.
Figure 6:
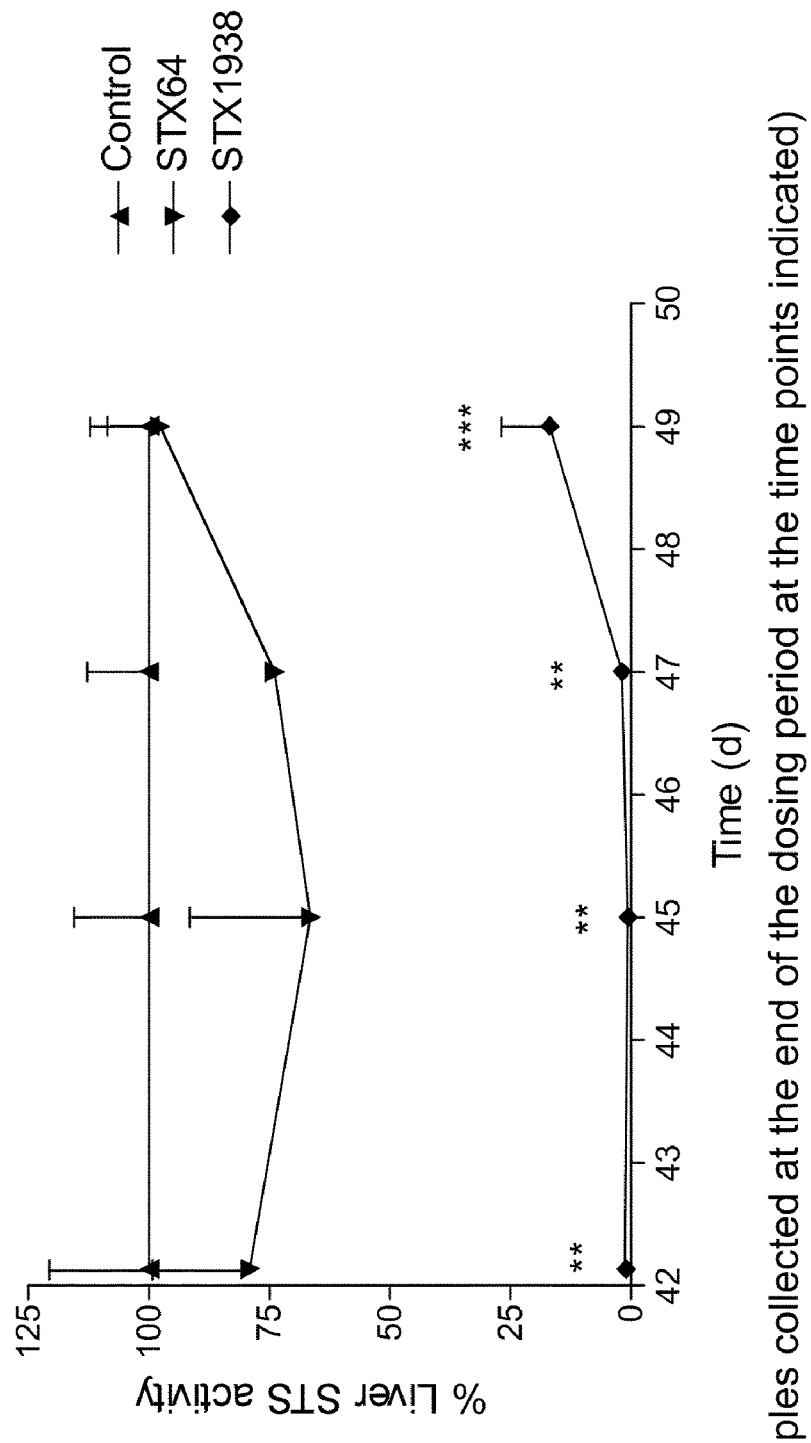
FIG. 6 shows the inhibition of liver STS by STX1938 or STX64 after weekly dosing.
Figure 7:
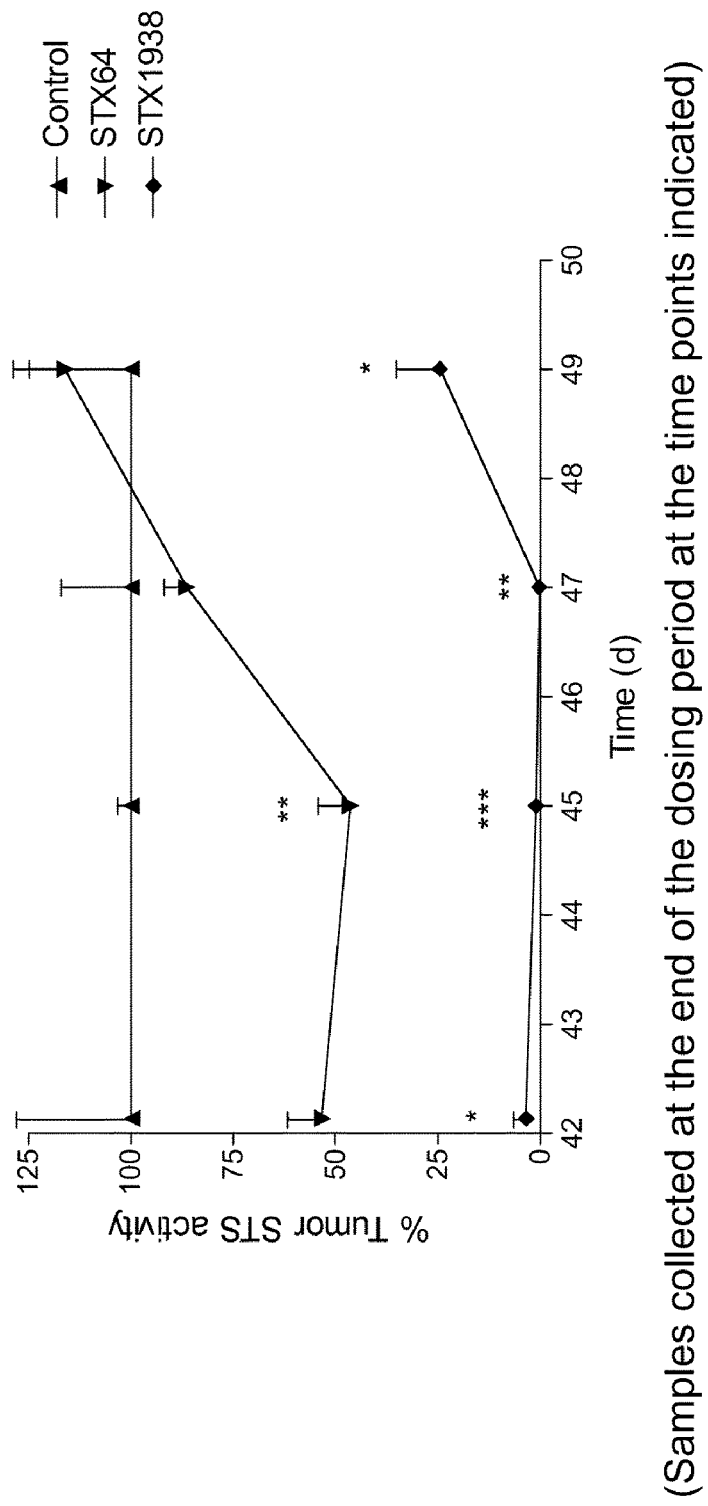
FIG. 7 shows the inhibition of tumour STS by STX1938 or STX 64 after weekly dosing.
Figure 8:
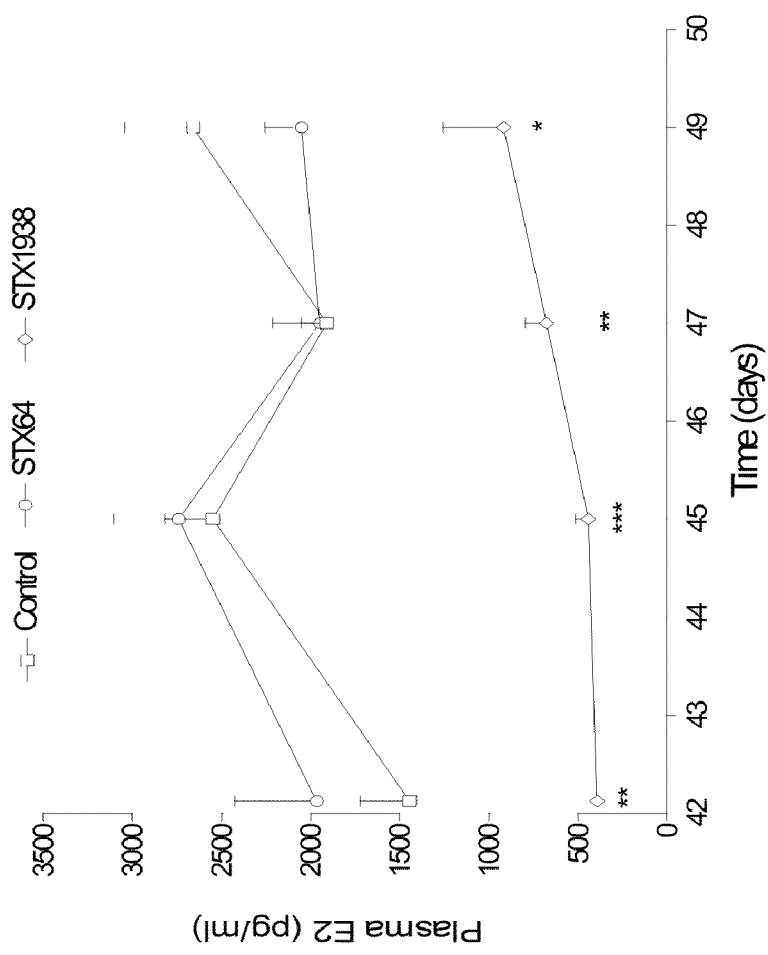
FIG. 8 shows reduction in plasma E2 levels after dosing at weekly intervals with STX1938 or STX64.

While dosing once per week with STX1938 significantly reduced tumour growth at this dosing schedule STX64 was ineffective (FIG. 5). Weekly dosing with STX1938 resulted in almost complete inhibition of tumour (FIG. 7) and liver (FIG. 6) STS. The activity of this enzyme continued to be inhibited for an extended period after the end of dosing. In contrast, STX64 at this dosing schedule only reduced liver and tumour STS activity by 25-50%. Plasma oestradiol levels were significantly reduced for an extended period after the cessation of dosing with STX1938 (FIG. 8).

Summary

STX1938 is a potent STS inhibitor which at doses of 1 mg/kg and 10 mg/kg significantly inhibits the growth of E2S-stimulated xenografts derived from MCF-7 breast cancer cells over expressing STS. Tumour STS activity is almost completely inhibited by STX1938.

STX1938 when given on a once per week dosing schedule is able to block the E2S-stimulated growth of xenograft tumours derived from MCF-7 cells over expressing STS. Tumour and liver STS activity is also completely inhibited. The greater efficacy of STX1938 over that of STX64 when administered weekly is thought to result from its longer duration of action than it has in vivo compared with that of STX64. This suggests that STX1938 will be suitable for developing as a once per week therapeutic agent.

All publications and patents and patent applications mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

Abbreviations
Å Angstrom
Ac Acetyl
Acc MS accurate mass spectrometry
Adiol androstenediol
Adione androstenedione
AG aminogluthethimide
aq aqueous
Ar aryl
arom aromatic
BMA 3-benzyl-marrianolic acid
Bn benzyl
br broad
° C. degrees Celsius
$^{13}$C NMR carbon NMR
ca approximately
cm centimeters
COUMATE 4-methylcoumarin-7-O-sulfamate
δ chemical shift in ppm
d doublet
dd doublet of doublets
DHEA dehydroepiandrosterone
DMF N,N-dimethylformamide
DMSO dimethylsulfoxide
E1 oestrone
E2 oestradiol
EMATE estrone-3-O-sulfamate
ER estrogen receptor
eq equivalent
FAB fast atom bombardment
g gram(s)
h hour(s)
hER human estrogen receptor
1H NMR proton NMR
HPLC high pressure liquid chromatography
17β-HSD 17β-hydroxysteroid dehydrogenase
Hz Hertz
$IC_{50}$ concentration causing 50% inhibition
IR infrared
J coupling constant in Hz
$\lambda_{max}$ wavelength of maximum absorption
lit. literature reference
μ micro
m multiplet
M mol per liter
m-NBA meta-nitrobenzyl alcohol
m-RNA messenger ribonucleic acid
MHz megahertz
min minute
mmol millimole
mol mole
mp melting point
MS mass spectrometry
m/z mass to charge ratio
NADPH nicotinamide adenine dinucleotide phosphate
nM nanomole
NMR nuclear magnetic resonance
ppm parts per million
$R_f$ retention factor
r.t. room temperature
S. D. standard deviation
Pd-C palladium-charcoal
TBAF tetrabutylammonium fluoride
TBDMS tert-butyl-dimethylsilyl
THF tetrahydrofuran
TLC thin layer chromatography
TMS tetramethylsilane
v frequency of a signal in Hz
vs. versus

REFERENCES (1) Saunders, C. M.; Baum, M. Management of early breast cancer. *Oncol. in Pract.* 1994, 3, 4-8
(2) Nicholls P. J. Breast cancer management: science and care together. *Pharm. J.* 1997, 259, 459-470
(3) Miller, B. A.; Kolonel, L. N.; Bernstein, L.; Young, Jr. J. L.; Swanson, G. M.; West, D.; Key, C. R.; Liff, J. M.; Glover, C. S.; Alexander, G. A.; et al. (eds). Racial/Ethnic patterns of cancer in the united states 1988-1992. *National Cancer Institute* 1996
(4) (a) Kaae, S. and Johansen, H. Does simple mastectomy followed by irradiation offer the survival comparable to radical procedures? *International Journal of Radiation Oncology, Biology, Physics.* 1977, 2, 1163-1166 (b) Holli, K.; Saaristo, R.; Isola, J.; Joensuu, H. and Hakama, M. Lumpectomy with or without postoperative radiotherapy for breast cancer with favourable prognostic features: results of a randomised study. *Br. J. Cancer* 2001, 84 (2), 164-169
(5) Early Breast Cancer Trialists' Collaborative Group. Effects of adjuvant Tamoxifen and of cytotoxic therapy on mortality in early breast cancer. *N. Eng. J. Med.* 1988, 319, 1681-1692
(6) Gorski, J.; Toft, D.; Shyamala, G.; Smith, D.; Notides, A. Hormones receptors: studies on the interaction of estrogens with the uterus. *Recent Prog. Horm. Res.* 1968, 24, 45-80
(7) Gorski, J. and Gannon F. Current models of steroid hormone action: a critique. *Ann. Rev. Physiol.* 1976, 38, 425-450
(8) Coulson, C. J. Steroid biosynthesis and action, $2^{nd}$ edition. *Molecular Mechanism of Drug Action.* 1994, 95-122
(9) (a) Horwitz, K. B. and McGuire, W. L. Nuclear mechanism of estrogen action: effects of oestradiol and antiestrogens on estrogens receptors and nuclear receptor processing. *J. Biol. Chem.* 1978, 253, 8185-8191 (b) Horwitz, K. B.; Koseki, Y. and McGuire, W. L. Oestrogen control of progesterone receptor in human breast cancer: role of oestradiol and antiestrogen. *Endocrinology* 1978, 103, 1742-1751

(10) (a) Jordan, V. C. The strategic use of antiestrogens to control the development and growth of breast cancer. *Cancer.* 1992, 70, 977-982 (b) Powles, T. J. Breast cancer prevention *Breast Cancer Res.* 2000, 2, 10-12

(11) Wakeling, A. E.; Bowler, J. Steroidal pure antiestrogens. *J. Endocrinol.* 1987, 112, R7-R10

(12) Sexton, M. J.; Gherman, R. B. Selective estrogen receptor modulators: the ideal estrogen replacement? *Prim. Care. Update Ob/Gyns* 2001, 8 (1), 25-30

(13) Agnusdei, D.; Liu-Leage, S.; Augendre-Ferrante, B. *Ann. Endocrinol.* 1999, 60 (3), 242-246

(14) John Smith, H.; Nicholls, P. J.; Simons, C.; Le Lain, R. Inhibitors of steroidogenesis as agents for the treatment of hormone-dependent breast cancer. *Exp. Opin. Ther. Patents* 2001, 11, 789-824

(15) (a) Castiglione-Gertsch, M. New aromatase inhibitors: more selectivity, less toxicity, unfortunately, the same activity. *Eur. J. Cancer* 1996, 32A, 393-395 (b) Miller, W. R. Aromatase inhibitors—where are we now? *Br. J. Cancer* 1996, 73, 415-417

(16) Santner, S. J.; Feil, P. D and Santen, R. J. In situ estrogen production via the oestrone sulphatase pathway in breast tumour: relative importance vs. the aromatase pathway. *J. Clin. Endocrin. Metab.* 1984, 59, 29-33

(17) Purohit, A. Williams, G. J.; Howarth, N. M.; Potter, B. V. L. and Reed, M. J. Inactivation of steroid sulphatase by an active site-directed inhibitor, estrone-3-O-sulfamate. *Biochem.* 1995, 34, 11508-11514

(18) Purohit, A.; Williams, G. J.; Roberts, C. J.; Potter, B. V. L.; Reed, M. J. In vivo inhibition of oestrone sulphatase and dehydroepiandrosterone sulphatase by estrone-3-O-sulfamate. *Int. J. Cancer* 1995, 62, 106-111

(19) Woo, L. W. L.; Howarth, N. M.; Purohit, A.; Hejaz, H. A. M.; Reed, M. J. and Potter, B. V. L. Steroidal and nonsteroidal sulfamates as potent inhibitors of steroid sulphatase. *J. Med. Chem.* 1998, 41, 1068-1083

(20) Purohit, A.; Woo, L. W. L.; Singh, A.; Winterborn, C. J.; Potter, B. V. L. and Reed, M. J. In vivo activity of 4-methylcoumarin-7-O-sulfamate, a non steroidal, non estrogenic steroid sulphatase inhibitor. *Cancer Res.* 1996, 56, 4950-4955

(21) (a) Woo, L. W. L.; Purohit, A.; Malini, B.; Reed, M. J. and Potter, B. V. L. Potent active site-directed inhibition of steroid sulphatase by tricyclic coumarin-based sulfamates. *Chemistry & Biology* 2000, 7, 773-791 (b) Malini, B.; Purohit, A.; Ganeshapillai, D.; Woo, L. W. L.; Potter, B. V. L.; Reed, M. J. Inhibition of steroid sulphatase activity by tricyclic coumarin sulfamates. *J. Steroid Biochem. Molec. Biol.* 2000, 75, 253-25 (c) Purohit, A.; Woo, L. W. L.; Barrow, D.; Hejaz, H. A. M.; Nicholson, R. I.; Potter, B. V. L.; Reed, M. J. Non-steroidal and steroidal sulfamates: new drugs for cancer therapy. *Mol. Cell. Endocrinol.* 2001, 171, 129-135

(22) Purohit, A.; Woo, L. W. L.; Potter, B. V. L.; Reed, M. J. In vivo inhibition of oestrone sulphatase activity and growth of nitrosomethylurea-induced mammary tumours by 667 COUMATE. *Cancer Res.* 2000, 60, 3394-3396

(23) Claussner, A.; Nédelec, L.; Nique, F.; Philibert, D.; Teush, G.; Van de Velde, P. 11β-Amidoalkylestradiols as new series of pure anti-estrogens. *J. Steroid. Biochem.* 1992, 41, 609-614

(24) Li, P-K.; Chu, G-C.; Guo, J. P.; Selcer, K. W. Development of potent non-estrogenic oestrone sulphatase inhibitors. *Steroids* 1998, 63, 425-432

(25) (a) Jin, J-Z.; Lin, S-X. Human estrogenic 17β-hydroxysteroid dehydrogenase: predominance of oestrone reduction and its induction by NADPH. *Biochem. Biophys. Res.* 1999, 259, 489-493 (b) Penning, T. M. Molecular endocrinology of hydroxysteroid dehydrogenases. *Endocrine Reviews* 1997, 18, 281-305

(26) (a) Labrie, F. At the cutting edge. Intracrinology. *Mol. Cell. Endocrinol.* 1991, 78, C113-C118 (b) Poulin, R.; Labrie, F. Stimulation of cell proliferation and estrogenic response by adrenal $C_{19}$-$?^5$-steroids in the ZR-75-1 Human Breast Cancer Cell Line. *Cancer Res.* 1986, 46, 4933-4937

(27) (a) Peltoketo, H.; Luu-The, V.; Simard, J.; Adamski, J. 17β-hydroxysteroid dehydrogenase (HSD)/17-ketosteroid reductase (KSR) family; nomenclature and main characteristics of the 17 HSD/KSR enzymes. *J. Mol. Endocrinol.* 1999, 23, 1-11 (b) Peltoketo, H.; Isomaa, V.; Maentausta, O.; Vihko, R. Complete amino acid sequence of human placental 17β-hydroxysteroid dehydrogenase deduced from cDNA. *FEBS Lett.* 1988, 239, 73-77 (c) Wu, L.; Einstein, M.; Geissler, W. M.; Chan, H. K.; Elliston, K. O.; Andersson, S. Expression cloning and characterization of human 17β-hydroxysteroid dehydrogenase type 2, a microsomal enzyme possessing 20α-hydroxysteroid dehydrogenase activity. *J. Biol. Chem.* 1993, 268, 12964-12969 (d) Geissler, W. M.; Davis, D. L.; Wu, L.; Bradshaw, K. D.; Patel, S.; Mendonca, B. B.; Elliston, K. O.; Wilston, J. D.; Russell, D. W.; Andersson, S. Male pseudohermaphroditism caused by mutation of testicular 17β-hydroxysteroid dehydrogenase 3. *Nat. Genet.* 1994, 7, 34-39 (e) Adamski, J.; Normand, T.; Leenders F.; Monte, D.; Begue, A.; Stehelin, D.; Jungblut, P. W.; de Launoit, Y. Molecular cloning of a novel widely expressed human 80 kDa 17β-hydroxysteroid dehydrogenase IV. *Biochem. J.* 1995, 311, 437-443 (f) Deyashiki, Y.; Ohshima, K.; Nakanishi, M.; Sato, K.; Matsuura, K.; Hara, A. Molecular cloning and characterization of mouse oestradiol 17β-dehydrogenase (A-specific), a member of the aldoketoreductase family. *J. Biol. Chem.* 1995, 270, 10461-10467

(28) Tremblay, M. R.; Auger, S, and Poirier, D. Synthesis of 16-(bromoalkyl)-estradiols having inhibitory effect on human placental oestradiol 17β-hydroxysteroid dehydrogenase (17β-HSD type 1). *Bioorg. Med. Chem.* 1995, 3, 505-523

(29) Tremblay, M. R.; Poirier, D. Overview of a rational approach to design type I 17β-hydroxysteroid dehydrogenase inhibitors without estrogenic activity: chemical synthesis and biological evaluation. *J. Steroid. Biochem.* 1998, 66, 179-191

(30) Collins, B. M.; Mac Lachlan, J. A.; Arnold, S. F. The estrogenic and anti-oestrogenic activities of phytochemicals with the human estrogen receptor expressed in yeast. *Steroids* 1997, 62, 365-372

(31) (a) Makela, S.; Poutanen, M.; Kostian, M. L.; Lehtimaki, N.; Strauss, L.; Santti, R.; Vihko, R. Inhibition of 17 beta-hydroxysteroid oxidoreductase by flavonoids in breast and prostate cancer cells. *Proc. Soc. Exp. Biol. Med.* 1998, 217, 310-316

(32) LeBail, J. C.; Laroche, T.; Marre-Fournier, F.; Habrioux, G. Aromatase and 17β-hydroxysteroid dehydrogenase inhibition by flavonoids. *Cancer Lett.* 1998, 133, 101-106

(33) Coldham, N. G.; James, V. H. T. A possible mechanism for increased breast cell proliferation by progestins through increased reductive 17β-hydroxysteroid dehydrogenase activity. *Int. J. Cancer* 1990, 45, 174-178
(34) Purohit, A.; Hejaz, H. A. M.; Walden, J.; MacCarthy-Marrogh, L.; Packam, G.; Potter, B. V. L.; Reed, M. J. The effect of 2-methoxyestrone-3-O-sulphamate on the growth of breast cancer cells and induced mammary tumours. *Int. J. Cancer* 2000, 85, 584-589
(35) Heer, J.; Miescher, K. Über Steroide. Marrianol-und Doisynolsäure. Über oestrogene carbonsäuren II. *Helv. Chim. Acta* 1945, 28, 156-165
(36) (a) Matkovics, B.; Taródi, B.; Baláspiri, L. Rearrangement of steroids, VII. Schmidt reaction and Beckmann rearrangement of oestrone and its derivatives. *Acta Chim. Acad. Scien. Hung.* 1974, 80, 79-87 (b) Regan, B. M.; Newton Hayes, F. 17- and 17-Aza-D-homosteroids. *J. Am. Chem. Soc.* 1956, 78, 639-643
(37) Gupta, R. and Jindal, D. P. Synthesis and biological activity of some D-ring modified oestrone derivatives. *Ind. J. Chem.* 1999, 38B, 563-571
(38) Love, B. and Dawson, C. R. Alkylphenols related to the poison ivy principle. An improved method of synthesis involving the Na-Butanol cleavage of benzyl ethers. *J. Am. Chem. Soc.* 1956, 78, 6095-6101
(39) Okada, M.; Iwashita, S.; Koizumi, N. Efficient general method for sulfamoylation of a hydroxyl group. *Tet. Lett.* 2000, 41, 7047-7051.
(40) C. A. Hioruchi & J. Y. Satoh, Regioselective 2-Iodination of Estradiol, Estriol & Oestrone, *J. Chem. Soc., Chem. Commun.*, 1982, 671-672.
(41) M. Numazawa and Y. Ogura, *J. Chem. Soc., Chem. Commun.* 1983, 9, 533.
(42) Williams, G. J.; Woo, L. W. L.; Mahon, M. F.; Purohit, A.; Reed, M. J.; Potter, B. V. L. X-ray crystal structure and mechanism of action of oestrone 3-O-sulphamate, a synthetic active site-directed inhibitor of oestrone sulphatase. *Pharm. Sci.* 1996, 2, 11-16
(43) Ghosh, D.; Pletnev, V. Z.; Zhu, D-W. et al. Structure of the human estrogenic 17 beta-hydroxysteroid dehydrogenase at 2.20 Å resolution. *Structure*, 1995, 3, 503-513
(44) (a) Lin, S. X.; Han, Q.; Azzi, A.; Zhu, D-W.; Gongloff, A.; Campbell, R. L. 3D structure of human estrogenic 17β-HSD: binding with various steroids. *J. Steroid Biochem. Mol. Biol.* 1999, 69, 425-429 (b) Puranen, T.; Poutanen, M.; Ghosh, D.; Vihko, R. and Vihko, P. Origin of substrate specificity of human and rat 17β-hydroxysteroid dehydrogenase Type 1, using chimeric enzymes and site-directed substitutions. *Endocrinology* 1997, 138, 3532-3539
(45) Breton, R.; Housset, D.; Mazza, C.; Fontecilla-Camps, J. C. The structure of a complex of human 17β-hydroxysteroid dehydrogenase with oestradiol and NADP+ identifies two principal targets for the design of inhibitors. *Structure* (Lond) 1996, 4, 905-915
(46) Apel, R.; Berger, G. Über das hydrazidosulfamid *Chem. Ber.* 1958, 91, 1339-1341
(47) Woo, L. W. W.; Lightowler, M.; Purohit, A.; Reed, M. J.; Potter, B. V. L. Heteroatom-substituted analogues of the active-site directed inhibitor estra-1,3,5(10)-trien-17-one-3-sulphamate inhibit oestrone sulphatase by different mechanism. *J. Steroid Biochem Mol. Biol.* 1996, 57, 79-88
(48) Duncan, L.; Purohit, A.; Howarth, N. M.; Potter, B. V. L.; Reed, M. J. Inhibition of oestrone sulphatase activity by estrone-3-methyl-thiophosphonate: a potential therapeutic agent in breast cancer *Cancer Res.* 1993, 53, 298-303.

The invention is further described by the following numbered paragraphs:

1. A compound having Formula I

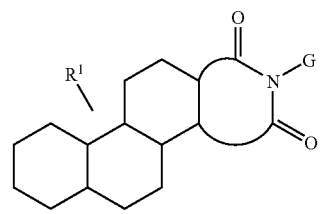

Formula I wherein G is a fluorocarbyl group, and wherein $R^1$ is any one of —OH, a sulphamate group, a phosphonate group, a thiophosphonate group, a sulphonate group or a sulphonamide group or a pharmaceutically acceptable salt or complex thereof.

2. A compound according to paragraph 1 having Formula II

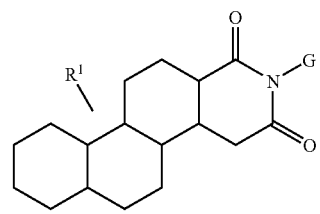

Formula II or a pharmaceutically acceptable salt or complex thereof.

3. A compound according to paragraph 1 having Formula III

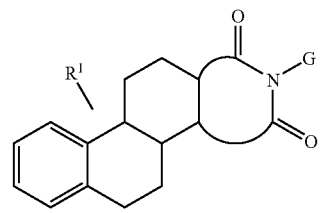

Formula III or a pharmaceutically acceptable salt or complex thereof.

4. A compound according to paragraph 1 having Formula IV

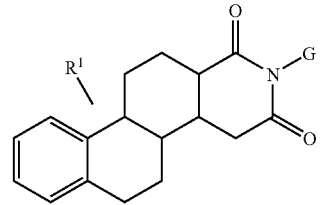

Formula IV or a pharmaceutically acceptable salt or complex thereof.

5. A compound according to paragraph 1 having Formula VII

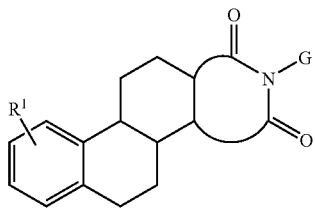

Formula VII or a pharmaceutically acceptable salt or complex thereof.

6. A compound according to paragraph 1 having Formula VIII

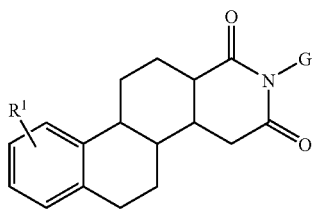

Formula VIII or a pharmaceutically acceptable salt or complex thereof.

7. A compound according to paragraph 1 having Formula XI

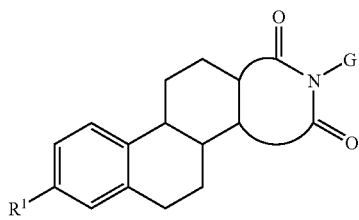

Formula XI or a pharmaceutically acceptable salt or complex thereof.

8. A compound according to paragraph 1 having Formula XII

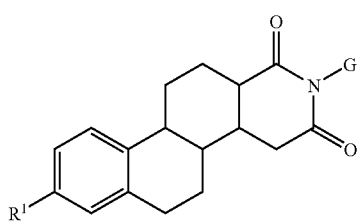

Formula XII or a pharmaceutically acceptable salt or complex thereof.

9. A compound according to any one of the preceding paragraphs wherein G is a group of the formula -A-B wherein A is a straight, branched or cyclic alkylene group of 1 to 9 carbon atoms, and B is a straight, branched or cyclic perfluoroalkyl group of from 1 to 10 carbon atoms or a pharmaceutically acceptable salt or complex thereof.

10. A compound according to paragraph 9 wherein A is a group of the formula $—(CH_2)_n—$ wherein n is an integer from 1 to 9 or a pharmaceutically acceptable salt or complex thereof.

11. A compound according to paragraph 9 or 10 wherein group A has two carbon atoms or a pharmaceutically acceptable salt or complex thereof.

12. A compound according to any one of paragraphs 9 to 11 wherein B is a group of the formula $—(CF_2)_mCF_3$ wherein m is 0 or an integer of from 1 to 9 or a pharmaceutically acceptable salt or complex thereof.

13. A compound according to paragraph 9 wherein group G has the formula $—(CH_2)_n(CF_2)_mCF_3$ wherein n is an integer from 1 to 9, m is 0 or integer from 1 to 9 or a pharmaceutically acceptable salt or complex thereof.

14. A compound according to paragraph 13 wherein n+m is between 1 and 10.

15. A compound according to any preceding paragraphs wherein group G is 3,3,3-trifluoropropyl ($—CH_2CH_2CF_3$) or a pharmaceutically acceptable salt or complex thereof.

16. A compound according to any one of the preceding paragraphs wherein $R^1$ is a sulphamate group or a pharmaceutically acceptable salt or complex thereof.

17. A compound according to paragraph 1 having the formula

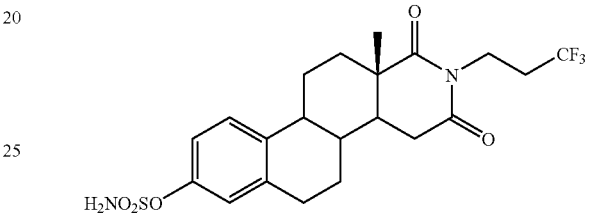

or a pharmaceutically acceptable salt or complex thereof.

18. A compound according to any one of the preceding paragraphs wherein $R^1$ or the sulphamate group is of the formula

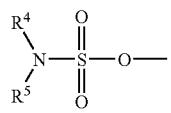

wherein $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups or a pharmaceutically acceptable salt or complex thereof.

19. A compound according to paragraph 18 wherein at least one of $R^4$ and $R^5$ is H or a pharmaceutically acceptable salt or complex thereof.

20. A compound according to paragraph 19 wherein $R^4$ and $R^5$ are H or a pharmaceutically acceptable salt or complex thereof.

21. A compound according to any one of the preceding paragraphs having Formula XII

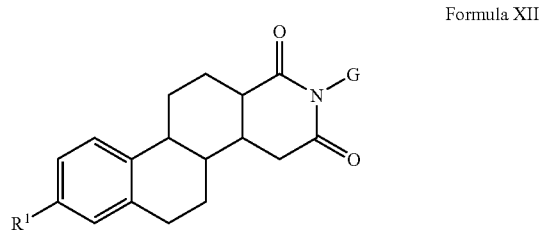

Formula XII wherein G is a fluorocarbyl group;

wherein $R^1$ is OH or a sulphamate group of the formula

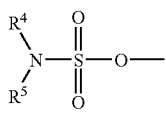

wherein $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups or a pharmaceutically acceptable salt or complex thereof.

22. A compound according to paragraph 21 having the formula

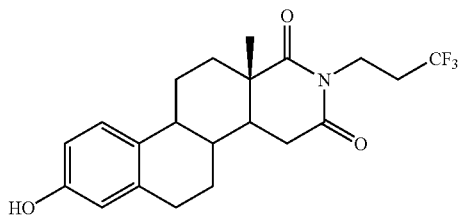

or a pharmaceutically acceptable salt or complex thereof.

23. A pharmaceutical composition comprising a compound according to any one of paragraphs 1 to 22 optionally admixed with a pharmaceutically acceptable carrier, diluent, excipient or adjuvant.

24. A compound according to any one of paragraphs 1 to 22 for use in medicine.

25. Use of a compound according to any one of paragraphs 1 to 22 in the manufacture of a medicament for use in the therapy of a condition or disease associated with steroid sulphatase (STS).

26. Use of a compound according to any one of paragraphs 1 to 22 in the manufacture of a medicament for use in the therapy of a condition or disease associated with adverse STS levels.

27. Use of a compound according to any one of paragraphs 1 to 22 in the manufacture of a pharmaceutical for inhibiting steroid sulphatase (STS) activity.

28. Use of a compound according to any one of paragraphs 1 to 22 in the manufacture of a pharmaceutical for inhibiting steroid sulphatase (STS) activity.

29. Use of a compound according to any one of paragraphs 1 to 22 in the manufacture of a pharmaceutical for the treatment of cancer.

30. Use according to paragraph 29 wherein the cancer is selected from endocrine dependent cancers.

31. Use according to paragraph 30 wherein the cancer is cancer of the breast, endometrium or prostate.

32. Use of a compound according to any one of paragraphs 1 to 22 in the manufacture of a pharmaceutical for treating a condition or disease associated with steroid sulphatase in a mammal in need thereof said treatment comprising administering to said mammal a pharmaceutically effective amount of a compound of the invention according to a schedule having a dosing interval of greater than daily.

33. Use according to paragraph 32 wherein the compound is administered as a unit dosage.

34. Use according to paragraph 32 wherein the dosage interval is selected from once weekly dosing, twice-weekly dosing, biweekly dosing, twice-monthly dosing and monthly dosing.

35. Use according to paragraph 32 wherein the dosage interval is once weekly dosing.

36. A compound as substantially hereinbefore described with reference to any one of the Examples.

37. A composition as substantially hereinbefore described with reference to any one of the Examples.

38. A method as substantially hereinbefore described with reference to any one of the Examples.

39. A use as substantially hereinbefore described with reference to any one of the Examples.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A compound having the formula

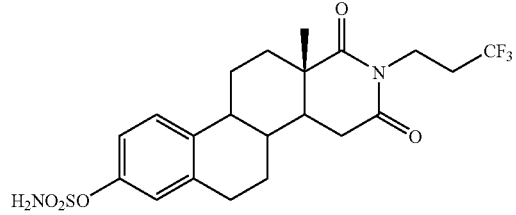

or a pharmaceutically acceptable salt thereof.

2. A pharmaceutical composition comprising a compound according to claim 1 optionally admixed with a pharmaceutically acceptable carrier, diluent, excipient or adjuvant.

3. A compound according to claim 1 for use in medicine.

\* \* \* \* \*